(12) United States Patent
Joseph et al.

(10) Patent No.: US 10,537,381 B2
(45) Date of Patent: Jan. 21, 2020

(54) SURGICAL INSTRUMENT HAVING A BIPOLAR END EFFECTOR ASSEMBLY AND A DEPLOYABLE MONOPOLAR ASSEMBLY

(71) Applicant: COVIDIEN LP, Mansfield, MA (US)

(72) Inventors: Daniel A. Joseph, Golden, CO (US); Gregory P. Hertrich, Longmont, CO (US); Jeremy P. Green, Westminster, CO (US); Dylan R. Kingsley, Broomfield, CO (US); Judd C. Nutting, Boulder, CO (US)

(73) Assignee: Covidien LP, Mansfield, MA (US)

( * ) Notice: Subject to any disclaimer, the term of this patent is extended or adjusted under 35 U.S.C. 154(b) by 456 days.

(21) Appl. No.: 15/055,260

(22) Filed: Feb. 26, 2016

(65) Prior Publication Data
US 2017/0245921 A1    Aug. 31, 2017

(51) Int. Cl.
*A61B 18/14*    (2006.01)
*A61B 18/00*    (2006.01)

(52) U.S. Cl.
CPC    *A61B 18/1445* (2013.01); *A61B 2018/00083* (2013.01); *A61B 2018/00601* (2013.01); *A61B 2018/1455* (2013.01)

(58) Field of Classification Search
CPC . A61B 18/14; A61B 18/1445; A61B 18/1447; A61B 2018/1475; A61B 2018/00607; A61B 17/00234
See application file for complete search history.

(56) References Cited

U.S. PATENT DOCUMENTS 4,005,714 A    2/1977    Hiltebrandt
D249,549 S    9/1978    Pike
(Continued)

FOREIGN PATENT DOCUMENTS

AU    2011253698 A1    12/2001
CN    21299462    9/2009
(Continued)

OTHER PUBLICATIONS

Extended European Search Report for application No. 17156975 dated Jul. 31, 2017.

*Primary Examiner* — Daniel W Fowler
*Assistant Examiner* — Tigist S Demie
(74) *Attorney, Agent, or Firm* — Carter, DeLuca & Farrell LLP

(57) ABSTRACT

A surgical instrument includes a housing, first, second, and third actuators operably coupled to the housing, an at least partially semi-rigid shaft extending distally from the housing, an end effector assembly disposed at a distal end of the shaft, and first, second, and third bars extending through the shaft in non-coaxial arrangement. The first bar is operably coupled between the first actuator and the end effector assembly such that actuation thereof effects manipulation of the end effector assembly. The second bar is operably coupled between the second actuator and a first deployable component such that actuation thereof effects deployment of the first deployable component relative to the end effector assembly. The third bar is operably coupled between the third actuator and a second deployable component such that actuation thereof effects deployment of the second deployable component relative to the end effector assembly.

18 Claims, 19 Drawing Sheets

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,026,379 A | 6/1991 | Yoon |
| D343,453 S | 1/1994 | Noda |
| 5,312,391 A | 5/1994 | Wilk |
| 5,318,589 A | 6/1994 | Lichtman |
| 5,324,254 A | 6/1994 | Phillips |
| D348,930 S | 7/1994 | Olson |
| D349,341 S | 8/1994 | Lichtman et al. |
| 5,342,359 A | 8/1994 | Rydell |
| 5,368,600 A | 11/1994 | Failla et al. |
| D354,564 S | 1/1995 | Medema |
| 5,401,274 A | 3/1995 | Kusunoki |
| D358,887 S | 5/1995 | Feinberg |
| 5,411,519 A | 5/1995 | Tovey et al. |
| 5,445,638 A | 8/1995 | Rydell et al. |
| 5,458,598 A | 10/1995 | Feinberg et al. |
| 5,527,313 A | 6/1996 | Scott et al. |
| 5,556,397 A | 9/1996 | Long et al. |
| 5,611,813 A | 3/1997 | Lichtman |
| D384,413 S | 9/1997 | Zlock et al. |
| 5,735,873 A | 4/1998 | MacLean |
| H1745 H | 8/1998 | Paraschac |
| 5,792,164 A | 8/1998 | Lakatos et al. |
| 5,807,393 A | 9/1998 | Williamson, IV et al. |
| D402,028 S | 12/1998 | Grimm et al. |
| D408,018 S | 4/1999 | McNaughton |
| 5,893,863 A | 4/1999 | Yoon |
| 5,919,202 A | 7/1999 | Yoon |
| 5,967,997 A * | 10/1999 | Turturro .............. A61B 10/06 600/567 |
| D416,089 S | 11/1999 | Barton et al. |
| 6,004,319 A | 12/1999 | Goble et al. |
| D424,694 S | 5/2000 | Tetzlaff et al. |
| D425,201 S | 5/2000 | Tetzlaff et al. |
| 6,113,596 A | 9/2000 | Hooven et al. |
| H1904 H | 10/2000 | Yates et al. |
| 6,156,009 A | 12/2000 | Grabek |
| 6,190,386 B1 | 2/2001 | Rydell |
| 6,270,497 B1 | 8/2001 | Sekino et al. |
| D449,886 S | 10/2001 | Tetzlaff et al. |
| 6,299,625 B1 | 10/2001 | Bacher |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,387,094 B1 | 5/2002 | Eitenmuller |
| H2037 H | 7/2002 | Yates et al. |
| 6,447,445 B1 * | 9/2002 | Hirano .............. A61B 1/0008 600/129 |
| D465,281 S | 11/2002 | Lang |
| D466,209 S | 11/2002 | Bon |
| 6,551,313 B1 | 4/2003 | Levin |
| 6,558,385 B1 | 5/2003 | McClurken et al. |
| 6,679,882 B1 | 1/2004 | Kornerup |
| D493,888 S | 8/2004 | Reschke |
| D496,997 S | 10/2004 | Dycus et al. |
| 6,808,525 B2 | 10/2004 | Latterell et al. |
| D499,181 S | 11/2004 | Dycus et al. |
| 6,837,888 B2 | 1/2005 | Ciarrocca et al. |
| D502,994 S | 3/2005 | Blake, III |
| D509,297 S | 9/2005 | Wells |
| 6,942,662 B2 | 9/2005 | Goble et al. |
| 7,033,356 B2 | 4/2006 | Latterell et al. |
| 7,063,699 B2 | 6/2006 | Hess et al. |
| D525,361 S | 7/2006 | Hushka |
| D531,311 S | 10/2006 | Guerra et al. |
| 7,128,254 B2 | 10/2006 | Shelton, IV et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| 7,208,005 B2 | 4/2007 | Frecker et al. |
| D541,611 S | 5/2007 | Aglassinger |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| 7,402,162 B2 | 7/2008 | Ouchi |
| D575,395 S | 8/2008 | Hushka |
| D575,401 S | 8/2008 | Hixson et al. |
| 7,442,194 B2 | 10/2008 | Dumbauld et al. |
| 7,445,621 B2 | 11/2008 | Dumbauld et al. |
| D582,038 S | 12/2008 | Swayer et al. |
| 7,481,810 B2 | 1/2009 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,577 B2 | 7/2010 | Nobis et al. |
| D621,503 S | 8/2010 | Otten et al. |
| 7,789,878 B2 | 9/2010 | Dumbauld et al. |
| 7,815,636 B2 | 10/2010 | Ortiz |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,879,035 B2 | 2/2011 | Garrison et al. |
| D649,249 S | 11/2011 | Guerra |
| D649,643 S | 11/2011 | Allen, IV et al. |
| D661,394 S | 6/2012 | Romero et al. |
| 8,257,352 B2 | 9/2012 | Lawes et al. |
| 8,333,765 B2 | 12/2012 | Johnson et al. |
| 8,353,437 B2 | 1/2013 | Boudreaux |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| RE44,834 E | 4/2014 | Dumbauld et al. |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |

(56) References Cited

U.S. PATENT DOCUMENTS

| | | |
|---|---|---|
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0113827 A1* | 5/2005 | Dumbauld .......... A61B 18/1445 606/45 |
| 2005/0187547 A1 | 8/2005 | Sugi |
| 2006/0129146 A1* | 6/2006 | Dycus ................ A61B 18/1445 606/51 |
| 2007/0078458 A1 | 4/2007 | Dumbauld et al. |
| 2007/0106295 A1* | 5/2007 | Garrison ............ A61B 18/1445 606/50 |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0215050 A1 | 9/2008 | Bakos |
| 2008/0243120 A1 | 10/2008 | Lawes et al. |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0009863 A1 | 1/2011 | Marczyk et al. |
| 2011/0071525 A1 | 3/2011 | Dumbauld et al. |
| 2011/0087218 A1 | 4/2011 | Boudreaux et al. |
| 2011/0130757 A1 | 6/2011 | Horlle et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0238016 A1* | 9/2013 | Garrison ................ A61B 17/29 606/205 |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0310865 A1* | 11/2013 | Merz ...................... A61B 17/32 606/170 |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1* | 1/2014 | Heard ................ A61B 18/1445 606/41 |
| 2014/0005666 A1* | 1/2014 | Moua .................... A61B 17/295 606/45 |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0100600 A1* | 4/2014 | Kendrick ............... A61B 17/29 606/205 |
| 2014/0257284 A1* | 9/2014 | Artale .................. A61B 18/1445 606/49 |
| 2014/0276797 A1 | 9/2014 | Batchelor et al. |

FOREIGN PATENT DOCUMENTS

| | | |
|---|---|---|
| CN | 201299462 | 9/2009 |
| DE | 2415263 A1 | 10/1975 |
| DE | 0251451 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |

(56) References Cited

FOREIGN PATENT DOCUMENTS

| | | |
|---|---|---|
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| EP | 2316367 A1 | 5/2011 |
| EP | 2853221 A1 | 4/2015 |
| EP | 2982326 A1 | 2/2016 |
| JP | 61-501068 | 9/1984 |
| JP | 10-24051 A | 1/1989 |
| JP | 11-47150 A | 6/1989 |
| JP | 65502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 3/1996 |
| JP | 08252263 A | 10/1996 |
| JP | 8-2989895 A | 11/1996 |
| JP | 8-317934 A | 12/1996 |
| JP | 8-317936 A | 12/1996 |
| JP | 9-10223 | 1/1997 |
| JP | 09000538 A | 1/1997 |
| JP | 9-122138 A | 5/1997 |
| JP | 2010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 2005/110264 A2 | 11/2005 |
| WO | 2006021269 A1 | 3/2006 |
| WO | 05110264 A3 | 4/2006 |
| WO | 2007118608 A1 | 10/2007 |
| WO | 08/040483 A1 | 4/2008 |
| WO | 2011/018154 A1 | 2/2011 |

\* cited by examiner

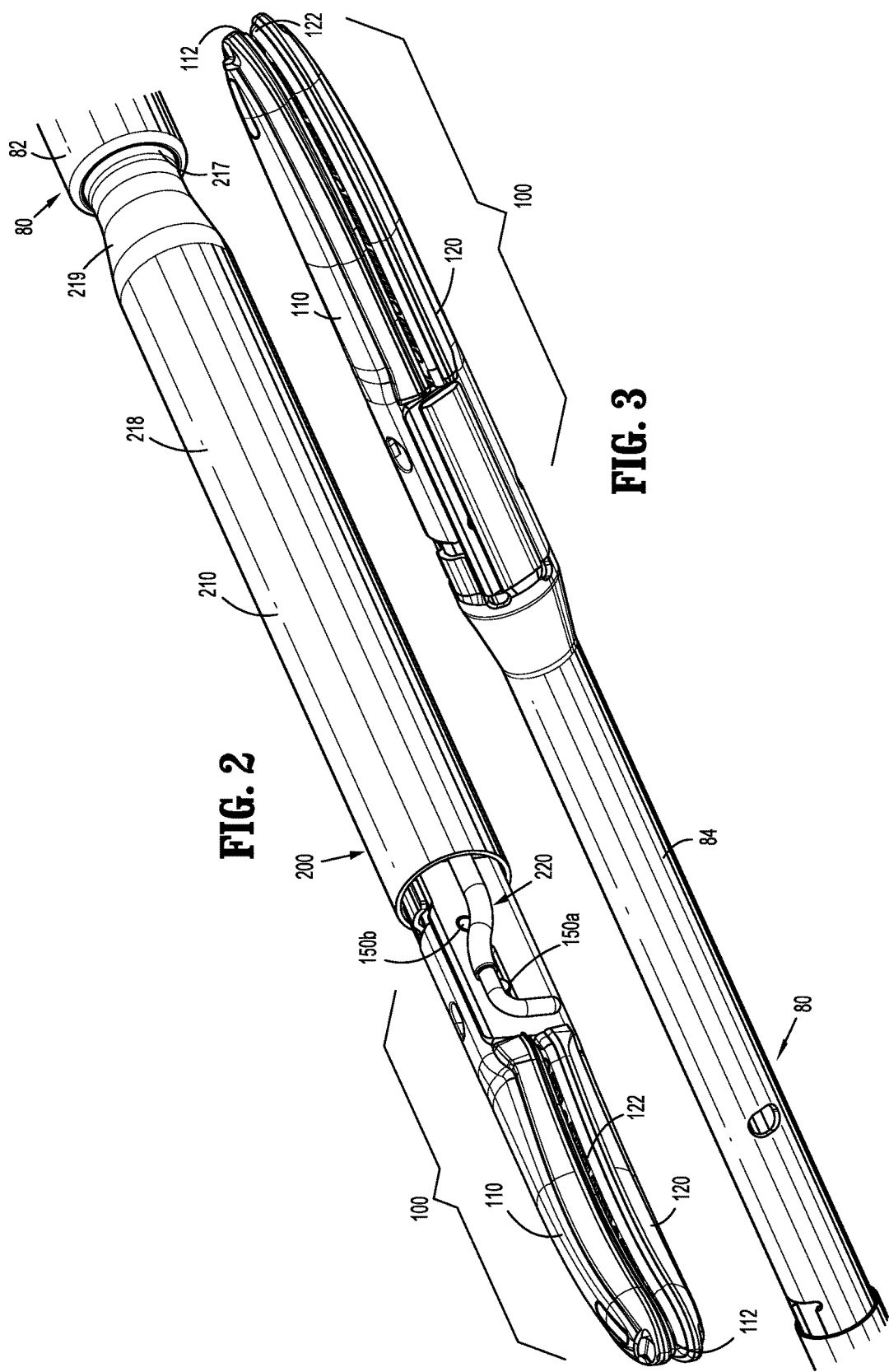

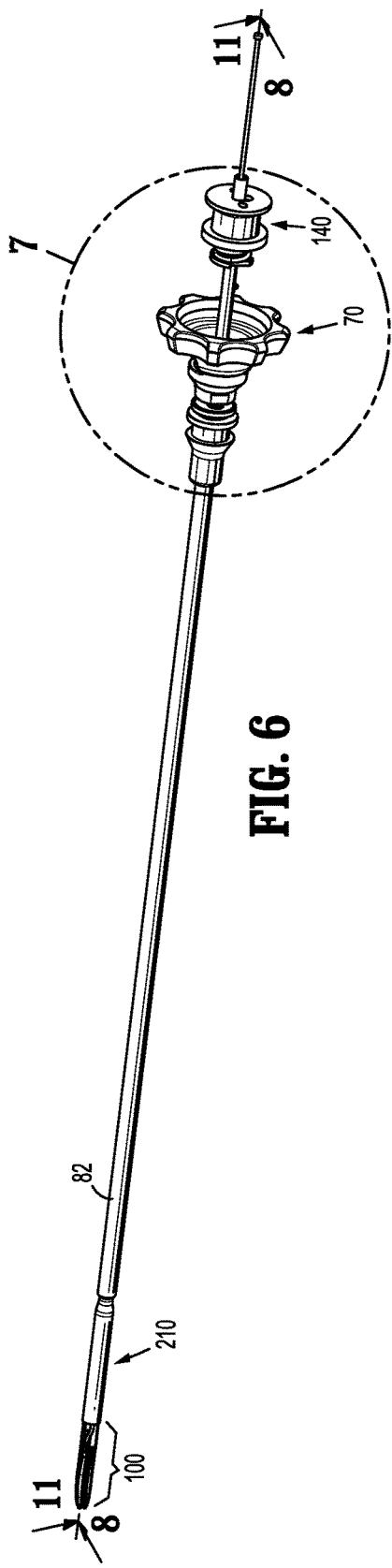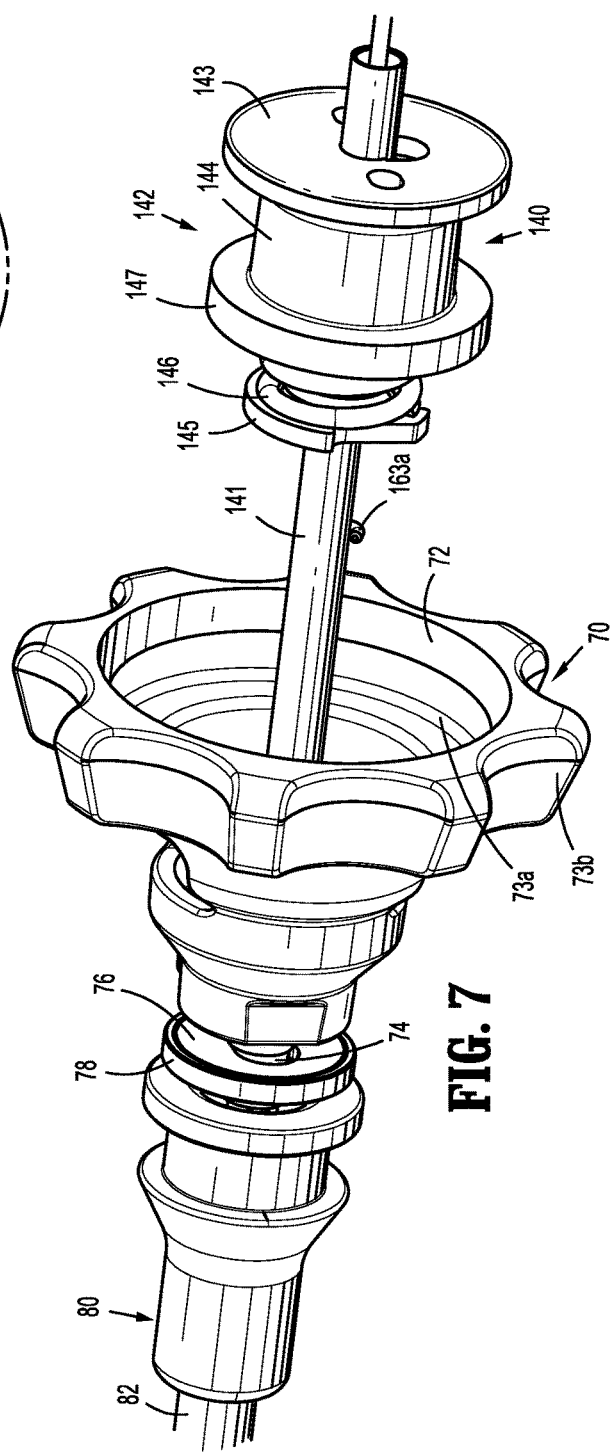

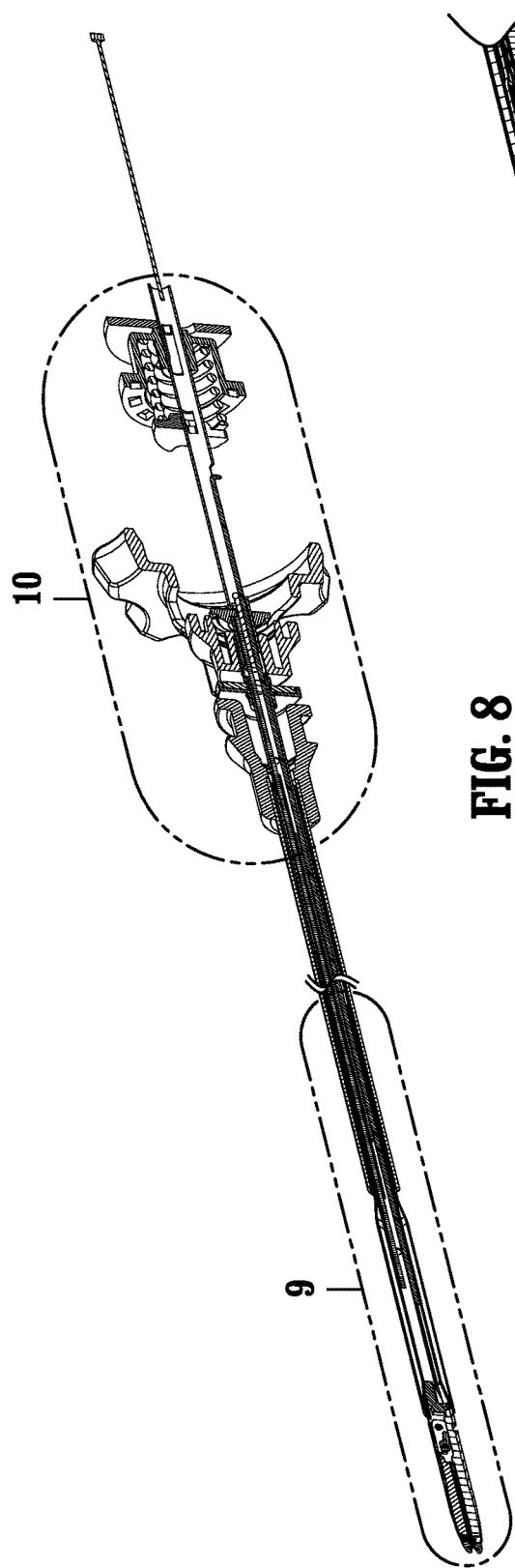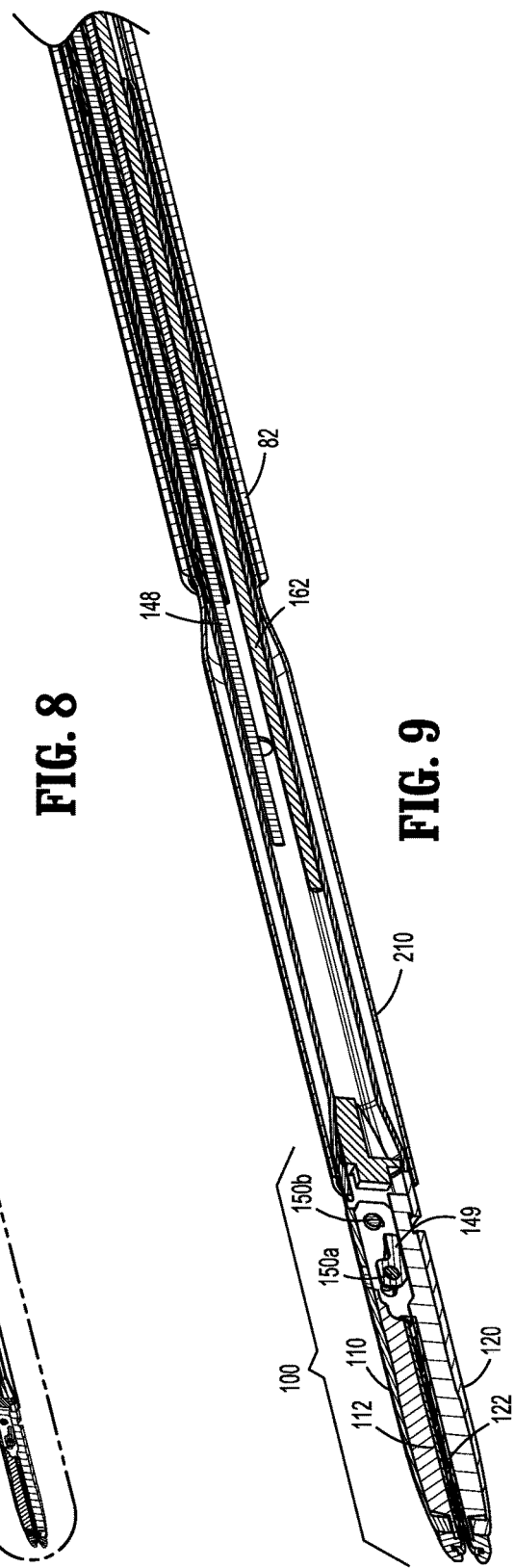

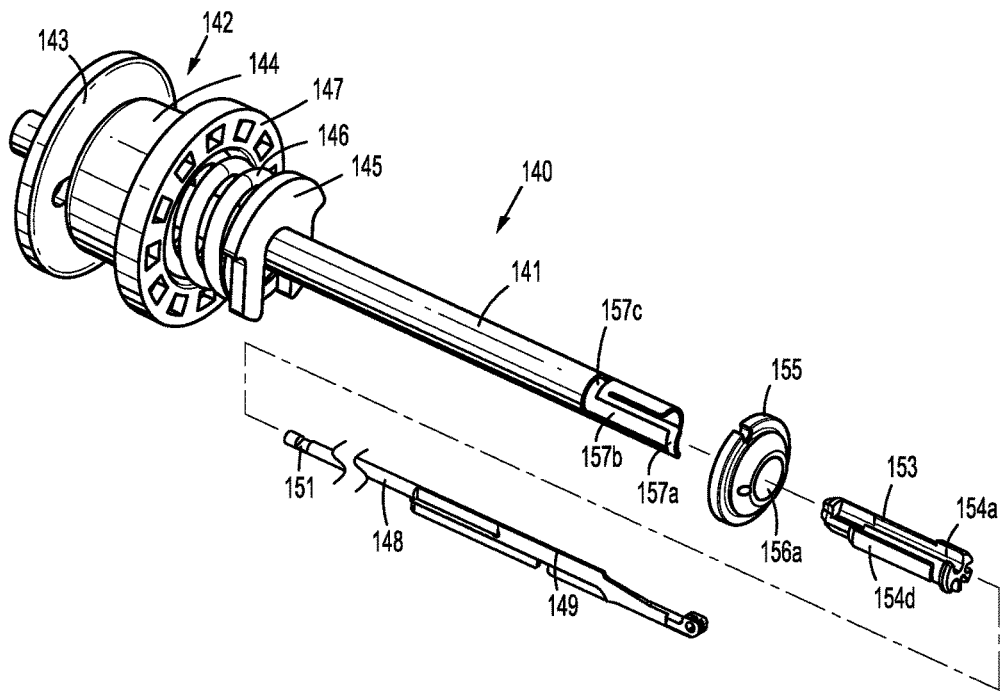
FIG. 14
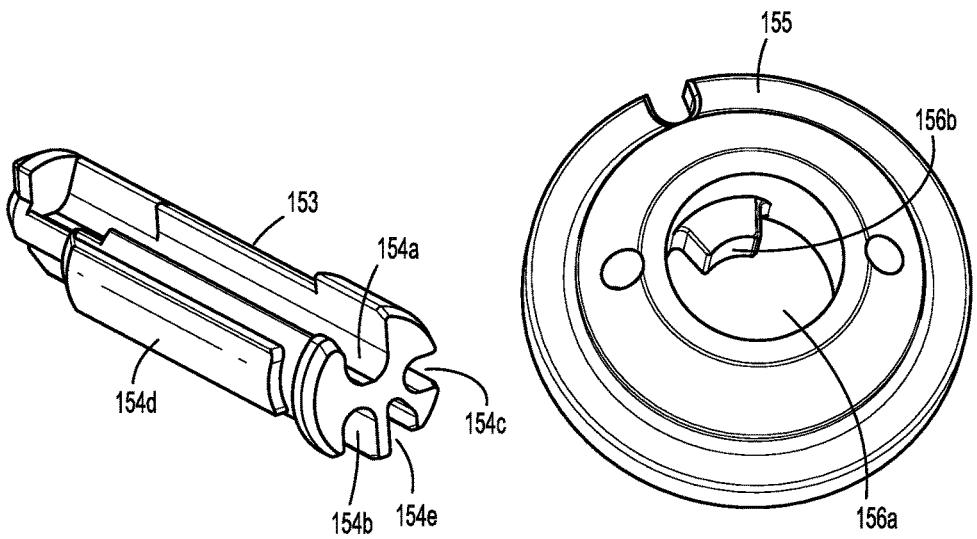
FIG. 15  FIG. 16

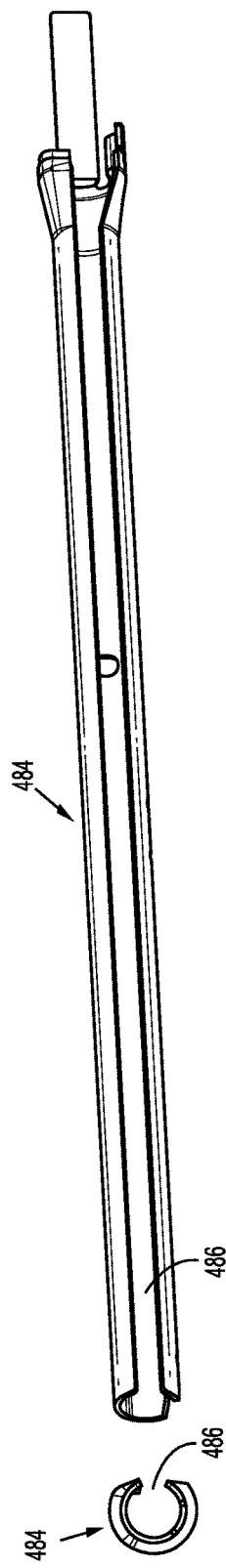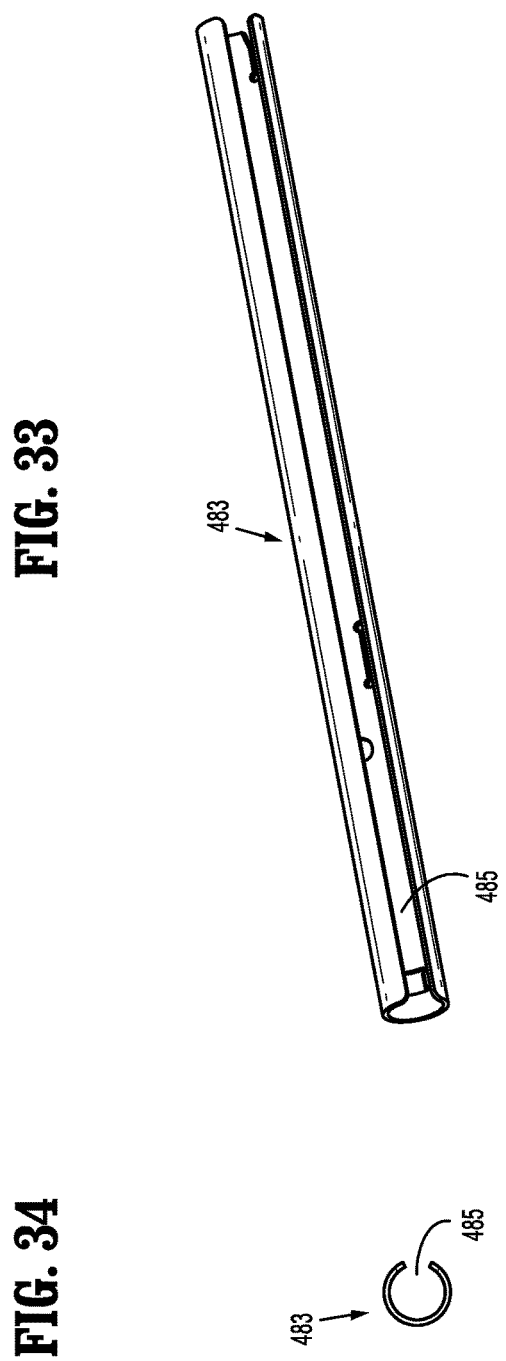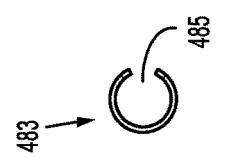

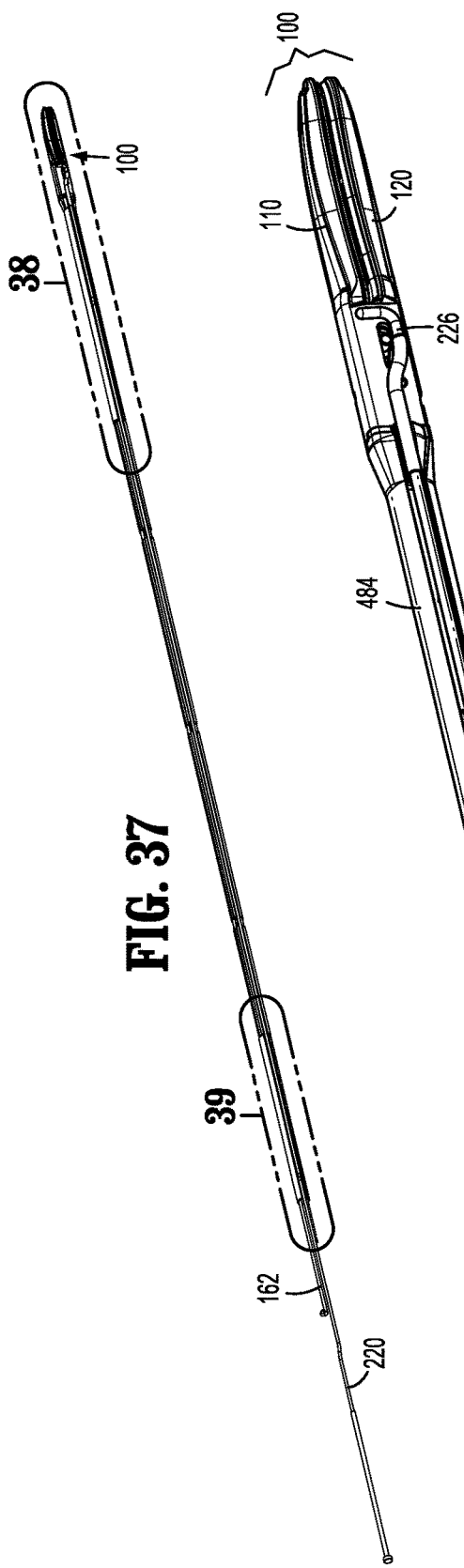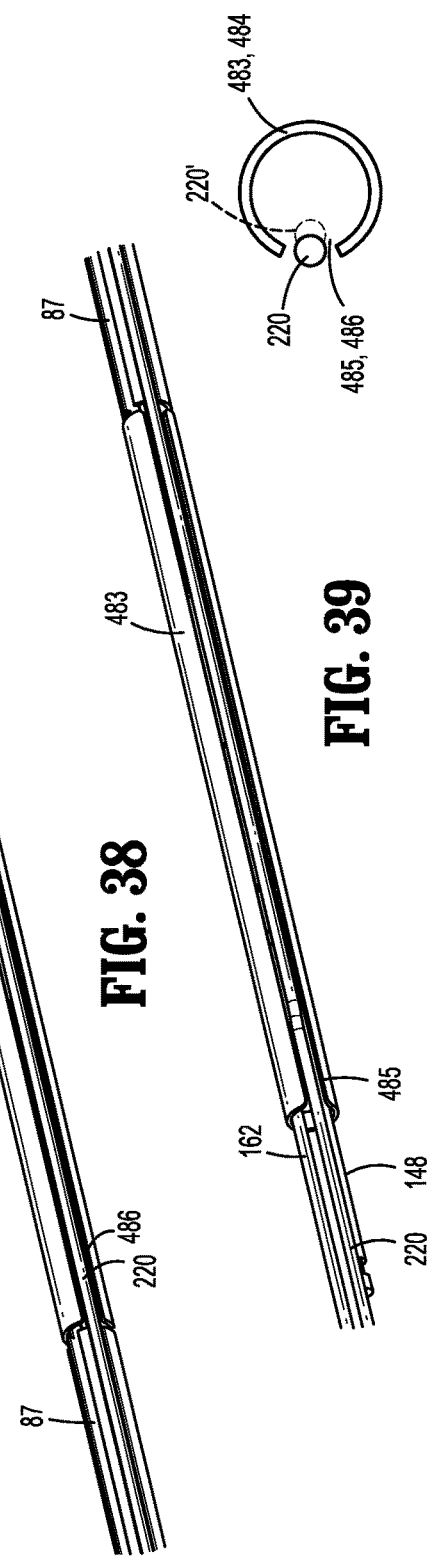

SURGICAL INSTRUMENT HAVING A BIPOLAR END EFFECTOR ASSEMBLY AND A DEPLOYABLE MONOPOLAR ASSEMBLY

BACKGROUND

Technical Field

The present disclosure relates to surgical instruments and, more particularly, to a multi-function surgical instrument including a bipolar end effector assembly and a deployable monopolar assembly.

Background of Related Art

Bipolar surgical instruments typically include two generally opposing electrodes charged to different electric potentials to selectively apply energy to tissue. Bipolar electrosurgical forceps, for example, utilize both mechanical clamping action and electrical energy to treat, e.g., cauterize, coagulate, desiccate, and/or seal, tissue. Once tissue is treated, it is often desirable to cut the treated tissue. Accordingly, many forceps have been designed which incorporate a knife that effectively severs the tissue after tissue treatment.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be treated. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

As can be appreciated, as additional functional components are added to a surgical instrument, additional deployment structures or deployment structures capable of actuating more than one component are required. However, multiple deployment structures and/or combined deployment structures may be limited by spatial constraints within the housing or shaft of the surgical instrument, functional constraints of the components, and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a surgical instrument including a housing, first, second, and third actuators operably coupled to the housing, an at least partially semi-rigid shaft extending distally from the housing, an end effector assembly disposed at a distal end of the shaft, and first, second, and third bars extending through the shaft and disposed in non-coaxial arrangement relative to each other and the shaft. The first bar is operably coupled between the first actuator and the end effector assembly such that actuation of the first actuator effects manipulation of the end effector assembly. The second bar is operably coupled between the second actuator and a first deployable component such that actuation of the second actuator effects deployment of the first deployable component relative to the end effector assembly. The third bar is operably coupled between the third actuator and a second deployable component such that actuation of the third actuator effects deployment of the second deployable component relative to the end effector assembly.

In an aspect of the present disclosure, the end effector assembly includes first and second jaw members adapted to connect to a source of energy for conducting energy through tissue. In such aspects, one or both of the jaw members is movable relative to the other between a spaced-apart position and an approximated position for grasping tissue therebetween.

In another aspect of the present disclosure, the first actuator includes a movable handle operably coupled to the housing and movable relative to the housing from an initial position to a compressed position to move the first and/or second jaw members from the spaced-apart position to the approximated position.

In another aspect of the present disclosure, the first deployable component is a knife selectively deployable between the first and second jaw members to cut tissue grasped therebetween.

In yet another aspect of the present disclosure, the second actuator includes a trigger operably coupled to the housing and movable relative to the housing from an un-actuated position to an actuated position to deploy the knife between the first and second jaw members.

In still another aspect of the present disclosure, the second deployable component includes an energizable member configured to conduct energy to tissue and movable relative to the end effector assembly between a retracted position, wherein the energizable member is positioned more-proximally, and an extended position, wherein the energizable member extends distally from the end effector assembly.

In another aspect of the present disclosure, an insulative sleeve is coupled to the energizable member and movable therewith such that the insulative sleeve is disposed proximally of the end effector assembly in the retracted position, and disposed about the end effector assembly in the extended position.

In still yet another aspect of the present disclosure, a proximal sleeve operably couples the first actuator and the first bar. In such aspects, the proximal sleeve and the shaft are co-axial.

In another aspect of the present disclosure, a guide member engages the proximal sleeve and the first bar. In such aspects, the guide member may define a first guide channel configured to retain a portion of the first bar, a second guide channel configured to slidably receive the second bar, and a third guide channel configured to slidably receive the third bar.

In yet another aspect of the present disclosure, a washer is operable to retain the guide member, proximal sleeve, and first bar in engagement with one another.

In another aspect of the present disclosure, a mandrel assembly is disposed about the proximal sleeve. In such aspects, the mandrel assembly operably couples the first actuator and the proximal sleeve, and the mandrel assembly, the proximal sleeve, and the shaft are co-axial.

In still another aspect of the present disclosure, a collar operably couples the second actuator and the second bar. In such aspects, the collar and the shaft are co-axial.

In still yet another aspect of the present disclosure, the shaft includes at least one support segment defining a first support channel for slidably receiving the first bar, a second support channel for slidably receiving the second bar, and a third support channel for slidably receiving the third bar.

In another aspect of the present disclosure, at least a portion of the shaft defines a cut-out therethrough. In such aspects, at least one of the first, second, or third bars extends at least partially into the cut-out.

In another aspect of the present disclosure, a rotation assembly is disposed about the shaft and operably coupled to the shaft and the first, second, and third bars such that rotation of the rotation assembly relative to the housing rotates the shaft, the end effector assembly, the first, second, and third bars, and the first and second deployable components relative to the housing. In such aspects, a clip and retainer may be configured to engage the rotation assembly about the shaft, or a G-shaped clip may be configured to engage the rotation assembly about the shaft.

In still another aspect of the present disclosure, a fixed outer tube is disposed about the shaft. In such aspects, the fixed outer tube and the shaft are co-axial.

In yet another aspect of the present disclosure, an insulative sleeve is slidably disposed between the fixed outer tube and the shaft. In such aspects, the insulative sleeve, fixed outer tube, and shaft are co-axial.

BRIEF DESCRIPTION OF THE DRAWINGS

Various aspects of the present disclosure are described herein with reference to the drawings wherein like reference numerals identify similar or identical elements and:

FIG. 2 is an enlarged, perspective view of the area of detail indicated as "2" in FIG. 1;

FIG. 3 is an enlarged, perspective view of the area of detail indicated as "3" in FIG. 1 from the opposite side as illustrated in FIG. 2, with portions removed;

FIG. 6 is a perspective view of the elongated shaft assembly of the surgical instrument of FIG. 1 and the components and assemblies coupled thereto;

FIG. 7 is an enlarged, perspective view of the area of detail indicated as "7" in FIG. 6;

FIG. 8 is a cross-sectional view taken along section line "8-8" of FIG. 7;

FIG. 9 is an enlarged, cross-sectional view of the area of detail indicated as "9" in FIG. 8;

FIG. 14 is an exploded, perspective view of the drive assembly of the surgical instrument of FIG. 1;

FIG. 15 is a perspective view of the drive bar support member of the drive assembly of FIG. 14;

FIG. 16 is a perspective view of the return washer of the drive assembly of FIG. 14;

FIG. 33 is a perspective view of the distal tube of another elongated shaft assembly configured for use with the surgical instrument of FIG. 1;

FIG. 34 is an front view of the distal tube of FIG. 33;

FIG. 35 is a perspective view of the proximal tube of the elongated shaft assembly of FIG. 33;

FIG. 36 is a front view of the proximal tube of FIG. 35;

FIG. 37 is a perspective view of the distal end of a surgical instrument incorporating the distal and proximal tubes of FIGS. 33 and 35, respectively, with portions removed;

FIG. 38 is an enlarged, perspective view of the area of detail indicated as "38" in FIG. 37;

FIG. 39 is an enlarged, perspective view of the area of detail indicated as "39" in FIG. 37; and FIG. 40 is a front view of the proximal tube of FIG. 35 illustrating positioning of an energizable member extending therethrough.

DETAILED DESCRIPTION

Figure 1:
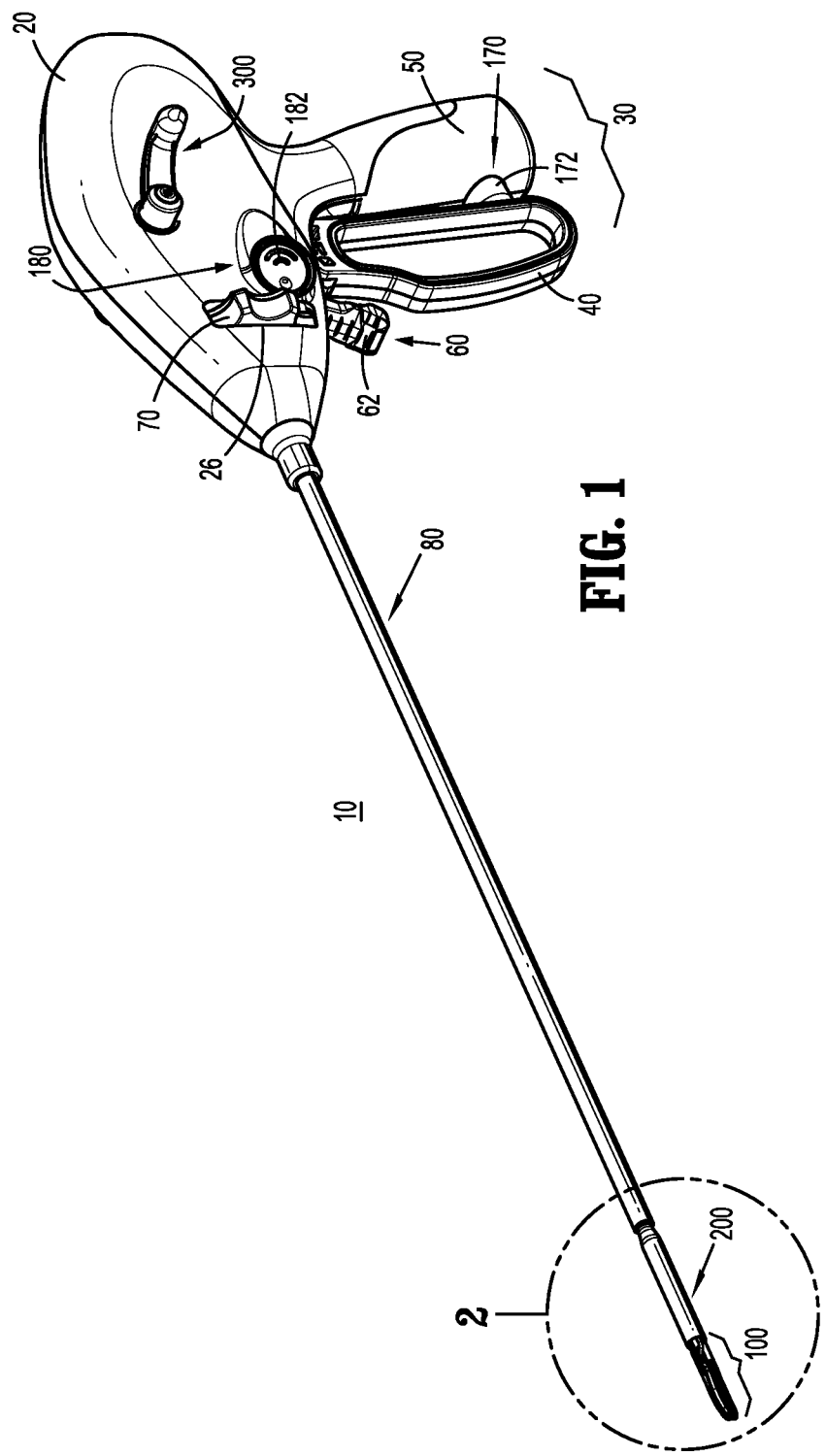
FIG. 1 is a perspective view of an endoscopic surgical instrument provided in accordance with the present disclosure with the monopolar assembly thereof disposed in a storage condition.

Referring generally to FIGS. 1-5, an endoscopic surgical instrument provided in accordance with the present disclosure is shown generally identified by reference numeral 10. Instrument 10, as described below, is configured to operate in both a bipolar mode, e.g., for grasping, treating, and/or mechanically dissecting tissue, and a monopolar mode, e.g., for treating and/or electrically/electromechanically dissecting tissue. Although the present disclosure is shown and described with respect to instrument 10, the aspects and features of the present disclosure are equally applicable for use with any suitable surgical instrument or portion(s) thereof. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1-5, instrument 10 generally includes a housing 20, a handle assembly 30, a trigger assembly 60, a rotation assembly 70, an elongated shaft assembly 80, an end effector assembly 100, a drive assembly 140, a knife assembly 160, bipolar and monopolar activation assemblies 170, 180, respectively, a monopolar assembly 200, and a deployment and retraction mechanism 300. As detailed below, elongated shaft assembly 80 extends distally from housing 20, supports end effector assembly 100 at a distal end thereof, drive assembly 140 operably couples handle assembly 30 with end effector assembly 100 to enable selective manipulation of jaw members 110, 120 of end effector assembly 100, knife assembly 160 is operably coupled with trigger assembly 60 to enable selective translation of knife 164 of knife assembly 160 relative to end effector assembly 100, and monopolar assembly 200 is operably coupled with deployment and retraction mechanism 300 to enable selective deployment and retraction of monopolar assembly 200. Rotating assembly 70 is operably coupled to elongated shaft assembly 80 and enables selective rotation of elongated shaft assembly 80, drive assembly 140, trigger assembly 60, end effector assembly 100, and monopolar assembly 200 relative to housing 20, as also detailed below. Bipolar and monopolar activation assemblies 170, 180 enable the appropriate energy to be selectively delivered to end effector assembly 100 and monopolar assembly 200, respectively.

Instrument 10 may also include an electrosurgical cable (not shown) that connects instrument 10 to a generator (not shown) or other suitable power source, although instrument 10 may alternatively be configured as a battery-powered instrument. The electrosurgical cable (not shown) includes wires (not shown) extending therethrough that have sufficient length to extend through housing 20 and/or elongated shaft assembly 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of the electrosurgical cable (not shown) extends through housing 20 and/or elongated shaft assembly 80 in order to provide energy to monopolar assembly 200, e.g., upon activation of either of the monopolar activation switches 182 of monopolar activation assembly 180 in the monopolar mode of operation.

Elongated shaft assembly 80 includes a fixed outer tube 82 having a proximal ferrule configured for engagement with housing 20 so as to engage fixed outer tube 82 therewith. Fixed outer tube 82 is a semi-rigid component in that it may be resiliently bent up to 35 degrees from a longitudinal axis thereof without permanent deformation or breaking. Fixed outer tube 82 does not extend distally to end effector assembly 100 but, rather, is spaced-apart therefrom, leaving an exposed section of monopolar assembly 200, although it is contemplated that, in some embodiments, fixed outer tube 82 extends to end effector assembly 100. Elongated shaft assembly 80 further includes a shaft having an inner proximal tube 83, an inner distal tube 84, and an inner tube guide 86 formed from a plurality of tube guide segments 87. Inner proximal tube 83 engages rotation assembly 70, as detailed below, and is disposed about a proximal portion of inner tube guide 86. Inner distal tube 84 engages jaw member 120 at the distal end thereof and is disposed about a distal portion of inner tube guide 86. The components of the shaft, e.g., inner proximal tube 83, inner distal tube 84, and inner tube guide 86, are engaged to one another in any suitable manner, e.g., welding, mechanical fastening, gluing, etc., to form the shaft of elongated shaft assembly 80 and such that rotation of inner proximal tube 83 effects corresponding rotation of inner distal tube 84 and inner tube guide 86. As a result, as will become apparent below, rotation of inner proximal tube 83 via rotation of rotation assembly 70 effects corresponding rotation of end effector assembly 100, drive assembly 140, knife assembly 160, and monopolar assembly 200 relative to housing 20 (FIG. 1) and fixed outer tube 82. At least inner tube guide 86 and, in some embodiments, inner proximal tube 83 and/or inner distal tube 84 are semi-rigid components, similarly as detailed above with respect to fixed outer tube 82, so as to enable resilient bending of elongated shaft assembly 80 up to 35 degrees from the longitudinal axis thereof without permanent deformation or breaking.

As detailed below, elongated shaft assembly 80 is configured to contain and/or support at least a portion of drive bar 148 of drive assembly 140, knife bar 162 of knife assembly 160, and energizable member 220 of monopolar assembly 200 in a non-concentric, non-coaxial arrangement, e.g., wherein drive bar 148, knife bar 162, and energizable member 220 extend alongside one another. Insulative sleeve 210 of monopolar assembly 200 is disposed about drive bar 148, knife bar 162, and energizable member 220 and is likewise non-concentrically and non-coaxially arranged about these components. Insulative sleeve 210 may be semi-rigid, similarly as detailed above, to enable bending. Further, drive bar 148, knife bar 162, and energizable member 220 are at least as flexible as the components of elongated shaft assembly 80, and define diameters significantly smaller than that diameters of the tubes 82, 83, 84, 86 of elongated shaft assembly 80 as well as insulative sleeve 210. For example, the diameters of drive bar 148, knife bar 162, and energizable member 220 may each be between one-third and one-tenth of the diameters of each or any of tubes 82, 83, 84, 86 and insulative sleeve 210. Such a configuration allows for deployment and/or actuation of end effector assembly 100 and monopolar assembly 200 even where elongated shaft assembly 80 (and the components extending therethrough) is resiliently bent up to 35 degrees from the longitudinal axis thereof.

Figure 5:
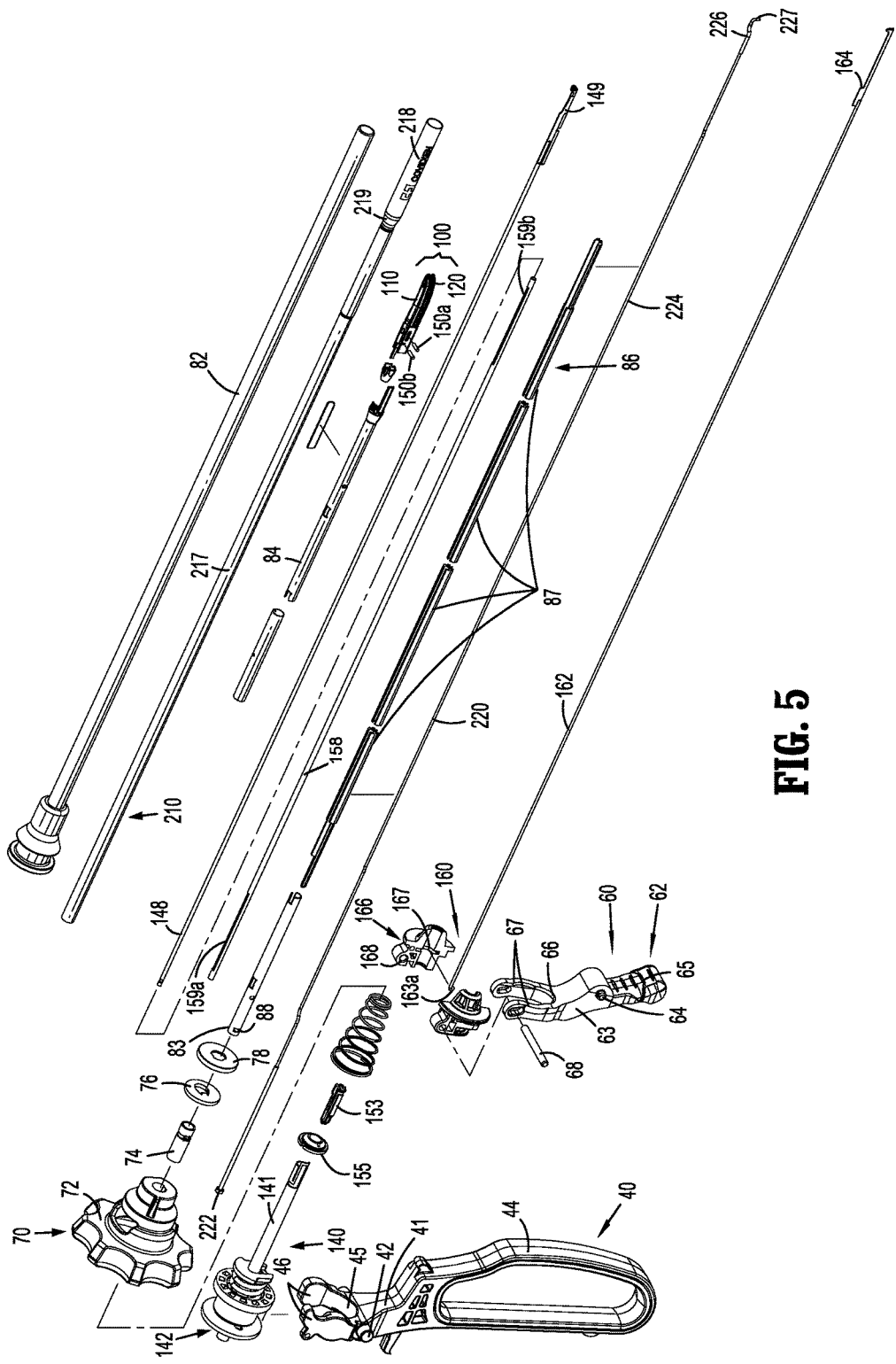
FIG. 5 is an exploded, perspective view of various operable assemblies of the surgical instrument of FIG. 1.
Figure 10:
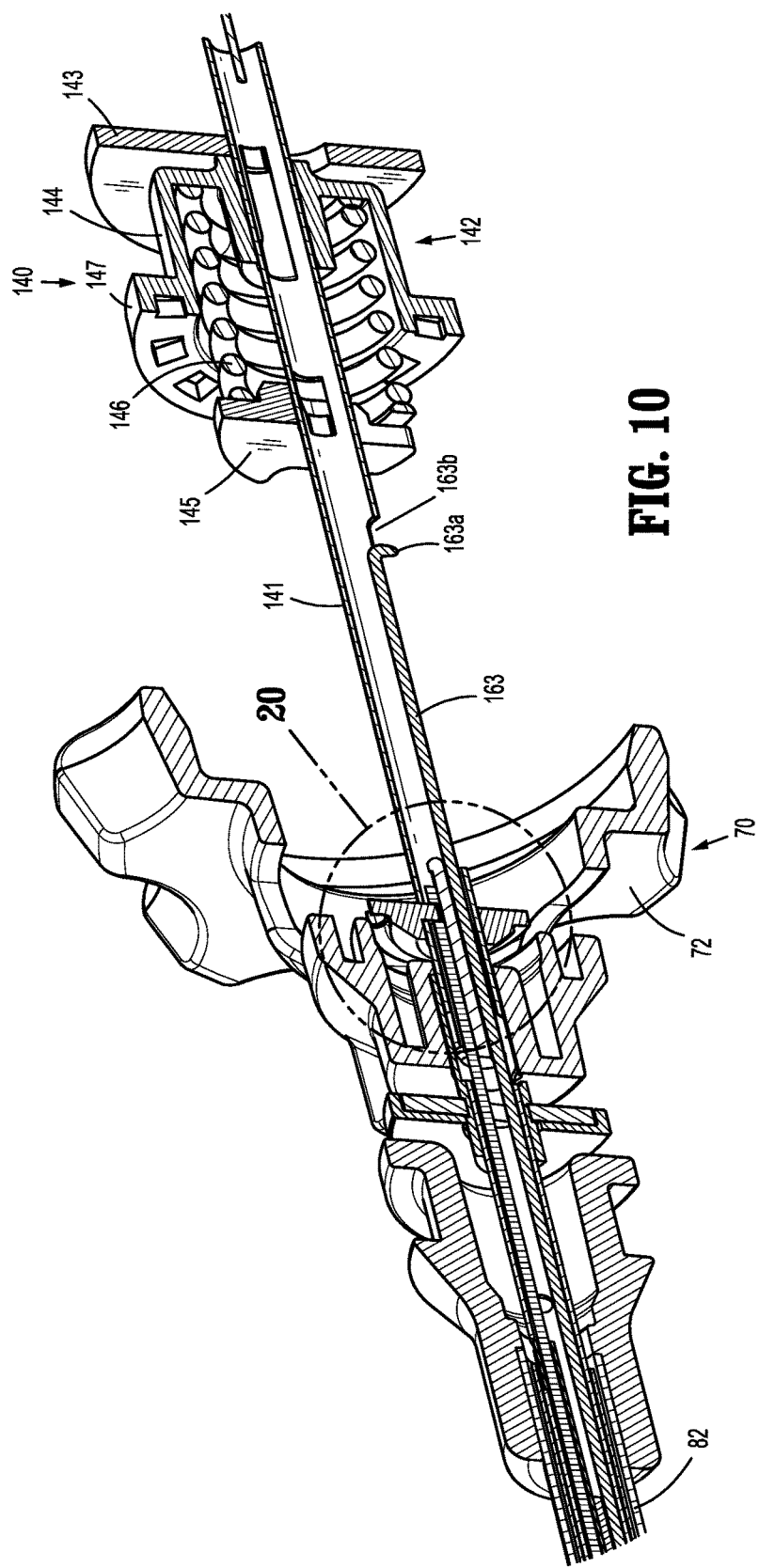
FIG. 10 is an enlarged, cross-sectional view of the area of detail indicated as "10" in FIG. 8.
Figure 11:
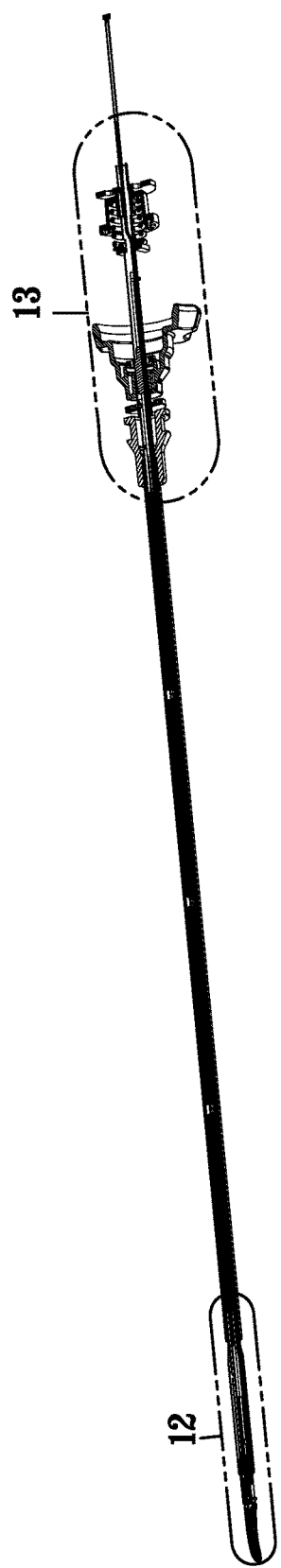
FIG. 11 is a cross-sectional view taken along section line "11-11" of FIG. 7.

With reference to FIGS. 2, 3, and 5, end effector assembly 100 is disposed at the distal end of elongated shaft assembly 80 and includes opposing jaw members 110, 120 pivotably coupled to one another. Each of the jaw members 110, 120 includes an electrically-conductive surface 112, 122. One or both of surfaces 112, 122 are adapted to connect to the source of energy (not shown), e.g., via the one or more wires (not shown), and are configured to conduct energy through tissue grasped therebetween to treat tissue, e.g., cauterize, coagulate/desiccate, and/or seal tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating tissue. Bipolar activation switch 172 of bipolar activation assembly 170 (FIG. 1) is operably coupled between the source of energy (not shown) and surfaces 112, 122 via one or more wires (not shown), thus allowing the surgeon to selectively apply energy to surfaces 112, 122 of jaw members 110, 120, respectively, of end effector assembly 100 during a bipolar mode of operation.

End effector assembly 100 is designed as a unilateral assembly, e.g., where jaw member 120 is fixed relative to elongated shaft assembly 80, e.g., jaw member 120 is engaged with inner distal tube 84 of elongated shaft assembly 80, and jaw member 110 is movable relative to elongated shaft assembly 80 and fixed jaw member 120. However, end effector assembly 100 may alternatively be configured as a bilateral assembly, i.e., where both jaw member 110 and jaw member 120 are movable relative to one another and to elongated shaft assembly 80. Further, in some embodiments, a longitudinally-extending knife channel 126 (FIG. 12) may be defined within one or both of jaw members 110, 120 to permit reciprocation of knife 164 (FIG. 5) therethrough, e.g., upon actuation of a trigger 62 of trigger assembly 60 (FIG. 5), to cut tissue grasped between jaw members 110, 120. Jaw members 110, 120 of end effector assembly 100 may otherwise be configured similar to or include any or all of the features of those of the end effector assembly detailed in U.S. Patent Application Publication No. 2014/0257274 to McCullough, Jr. et al., filed on Mar. 4, 2014, the entire contents of which are hereby incorporated herein by reference.

Figure 4:
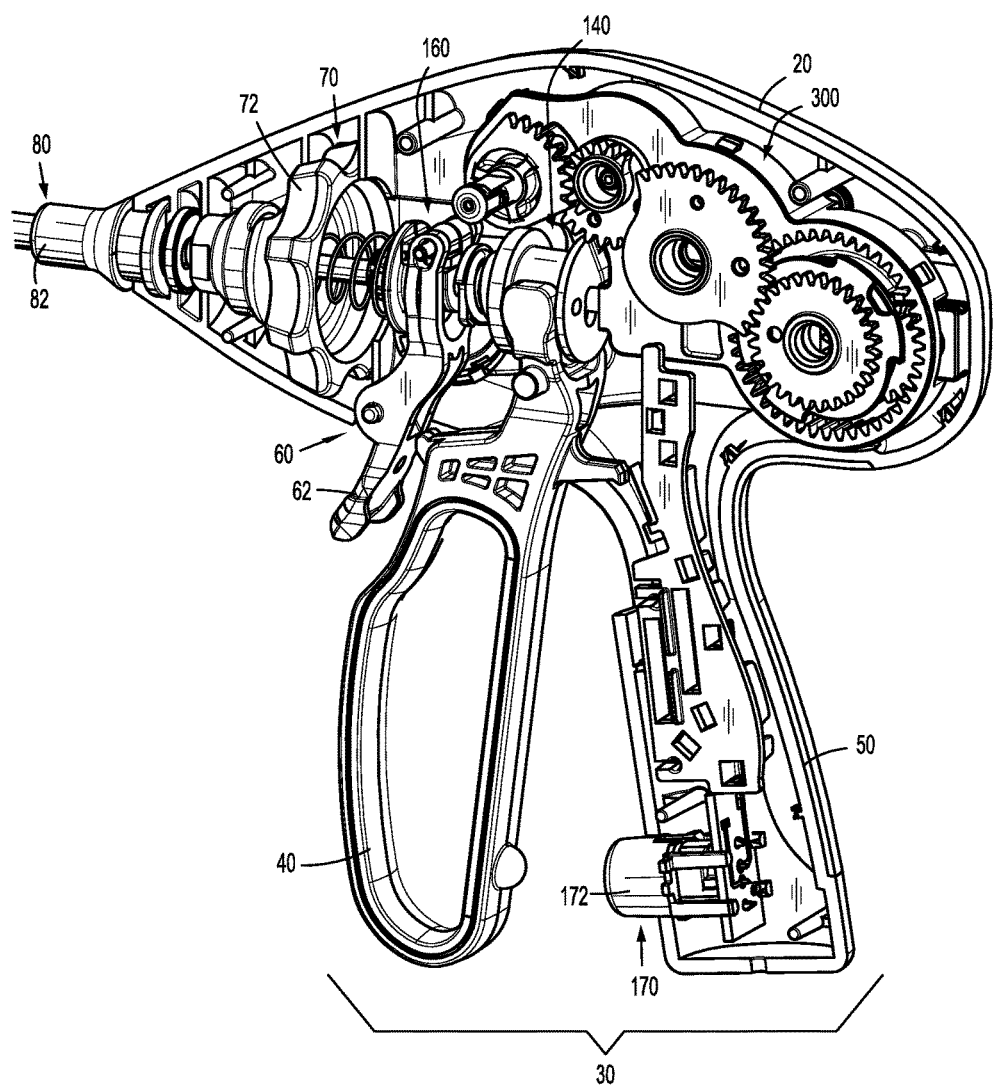
FIG. 4 is a perspective view of the proximal end of the surgical instrument of FIG. 1 with portions removed to illustrate the internal working components thereof.

Referring to FIGS. 1, 4, and 5, handle assembly 30 includes movable handle 40 and a fixed handle 50. Fixed handle 50 is integrally associated with housing 20 and movable handle 40 is movable relative to fixed handle 50 between an initial position, wherein movable handle 40 is spaced-apart from fixed handle 50, and a compressed position, wherein movable handle 40 is compressed towards fixed handle 50. More specifically, an intermediate portion 41 of movable handle 40 is pivotably coupled within housing 20 on either side of housing 20 via a split pivot 42. A grasping portion 44 of movable handle 40 extends from split pivot 42 in a first direction, ultimately exiting housing 20 to facilitate grasping and manipulation of movable handle 40 from the exterior of housing 20. A bifurcated portion 45 of movable handle 40 extends from split pivot 42 in a second, opposite direction further into housing 20. Bifurcated portion 45 of movable handle 40 includes a pair of spaced-apart flanges 46.

With reference to FIGS. 5, 7, 10, 13, and 14, drive assembly 140 includes a proximal sleeve 141 that is slidably disposed within housing 20 (see FIG. 4) and configured to operably couple to movable handle 40. Proximal sleeve 141 is coaxial relative to elongated shaft assembly 80 (e.g., tubes 82, 83, 84, 86); however, as detailed below, drive bar 148 of drive assembly 140 is non-coaxial relative to elongated shaft assembly 80. A mandrel assembly 142 of drive assembly 140 operably couples movable handle 40 with proximal sleeve 141 of drive assembly 140. Mandrel assembly 142 is coaxial with proximal sleeve 141 and elongated shaft assembly 80 and includes a proximal collar 143 that is fixedly engaged about proximal sleeve 141, a mandrel 144 slidably disposed about proximal sleeve 141 and positioned distally of proximal collar 143, and a clip 145 engaged about proximal sleeve 141 distally of mandrel 144 such that mandrel 144 is slidably retained between proximal collar 143 and clip 145. A biasing member 146 is positioned about proximal sleeve 141 between mandrel 144 and clip 145 so as to bias mandrel 144 proximally along proximal sleeve 141. Biasing member 146 defines a length such that biasing member 146 is pre-loaded, even when mandrel 144 is in a proximal-most position. Mandrel 144 includes a distal washer 147 integrally formed therewith (although other suitable engagements are also contemplated) so as to define an annular recess between distal washer 147 of mandrel 144 and proximal collar 143 for receipt of spaced-apart flanges 46 of movable handle 40 on either side of mandrel 144. Proximal collar 143, mandrel 144, biasing member 146, and clip 145 may be assembled on proximal sleeve 141 and relative to one another similarly as detailed in U.S. Patent Application Pub. No. 2014/0025071 to Sims et al., filed on Sep. 25, 2013, the entire contents of which are hereby incorporated herein by reference. This assembly method obviates the need for precision joining, such as welding, to achieve proper positioning and spacing between the components.

Figure 12:
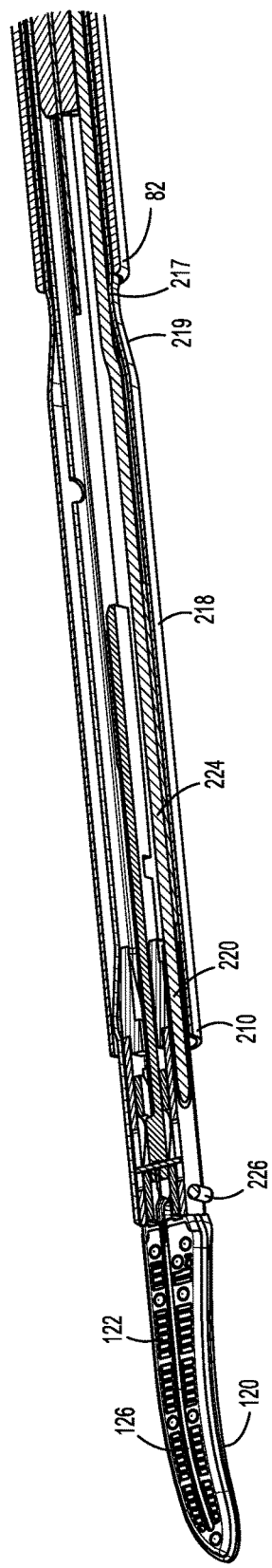
FIG. 12 is an enlarged, cross-sectional view of the area of detail indicated as "12" in FIG. 11.
Figure 13:
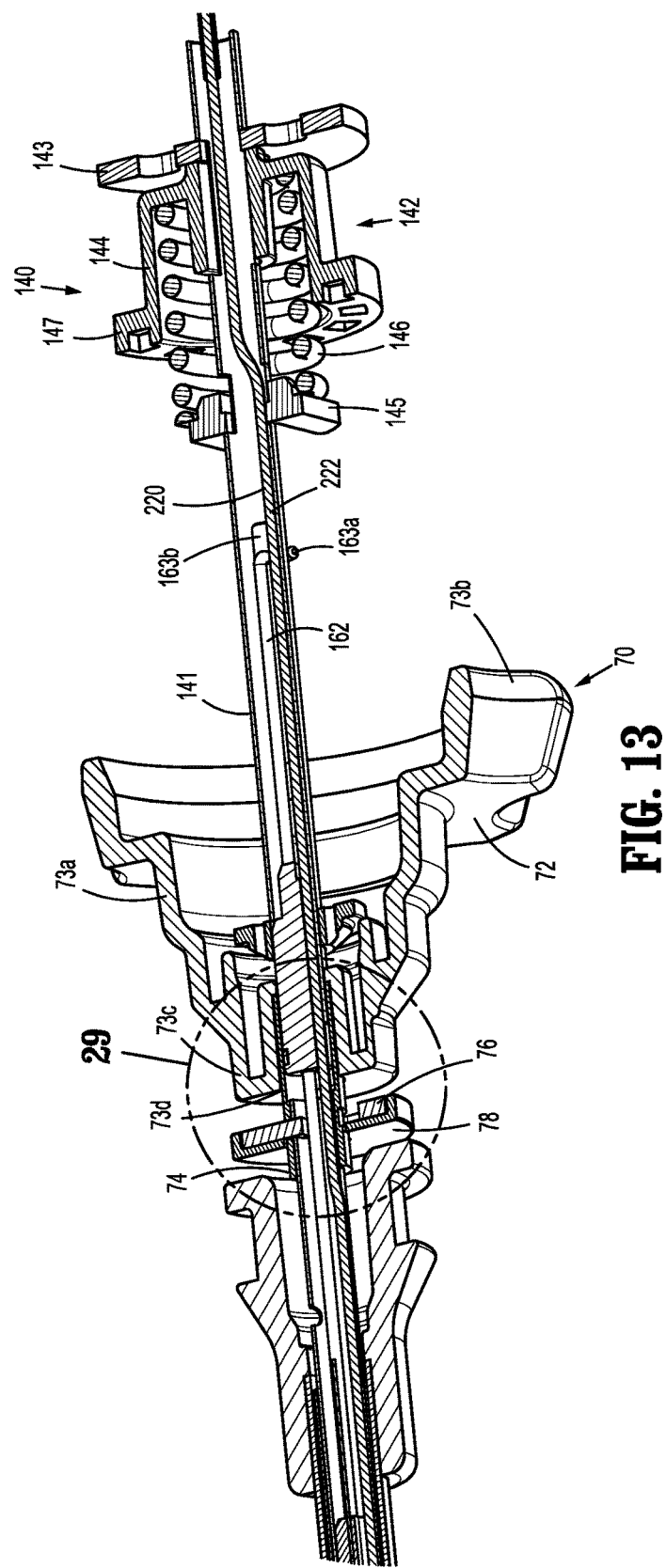
FIG. 13 is an enlarged, cross-sectional view of the area of detail indicated as "13" in FIG. 11.

Referring to FIGS. 5, 9, 12, and 14, drive assembly 140 further includes a drive bar 148 operably coupled to end effector assembly 100 at the distal end of drive bar 148 and operably coupled to proximal sleeve 141 at the proximal end of drive bar 148. More specifically, drive bar 148 defines an arm 149 at the distal end thereof that is configured to receive a cam pin 150a (FIGS. 5, 9, and 12). Cam pin 150a, in turn, is received within corresponding cam slots defined within jaw members 110, 120 such that translation of drive bar 148 relative to end effector assembly 100 translates cam pin 150a through the cam slots to thereby pivot jaw member 110 relative to jaw member 120 about pivot pin 150b (see FIGS. 5, 9, and 12). In particular, distal translation of drive bar 148 urges jaw member 110 to pivot towards the approximated position, while proximal translation of drive bar 148 urges jaw member 110 to pivot towards the spaced-apart position, although the opposite configuration is also contemplated. 158

Drive bar 148 defines a notch 151 therein towards the proximal end thereof that is configured, in conjunction with a drive bar support member 153 and return washer 155, to facilitate operable coupling of drive bar 148 with proximal sleeve 141. Drive assembly 140 further includes a support tube 158 disposed about drive bar 148. Support tube 158 extends about drive bar 148 but defines a shorter length than drive bar 148 such that the distal end of support tube 158 is position proximally of arm 149 and such that the proximal end of support tube 158 is positioned distally of notch 151. Support tube 158 defines a proximal slot 159a and a distal slot 159b. Support tube 158 and drive bar 148 are configured for receipt within a channel defined within inner guide tube 86 of elongated shaft assembly 80 (see FIG. 5).

With reference to FIGS. 14 and 15, drive bar support member 153 defines a drive bar channel 154a configured to receive a portion of drive bar 148, a energizable member channel 154b configured to slidably receive a portion of energizable member 220 (see FIG. 21), a knife bar channel 154c configured to slidably receive a portion of knife bar 162 (see FIG. 21), and an elongated protrusion 154d defining a generally rectangular configuration. Drive bar support member 153 may further define a wire guide channel 154e configured to receive the wires (not shown) extending to jaw members 110, 120 of end effector assembly 100 (FIGS. 2 and 3).

Referring to FIGS. 14 and 16, return washer 155 defines a central aperture 156a and a locking finger 156b extending inwardly into central aperture 156a.

Figure 17:
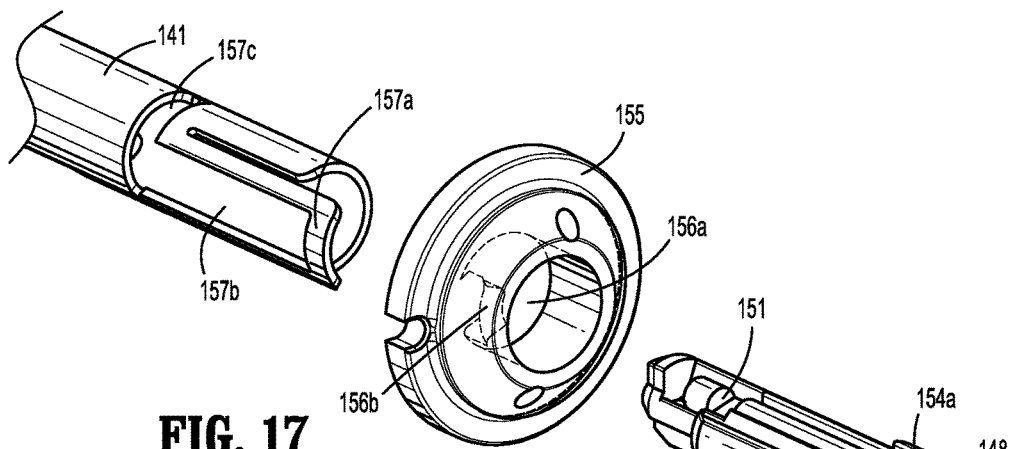
FIG. 17-19 are perspective views illustrating assembly of the drive assembly of FIG. 14.
Figure 18:
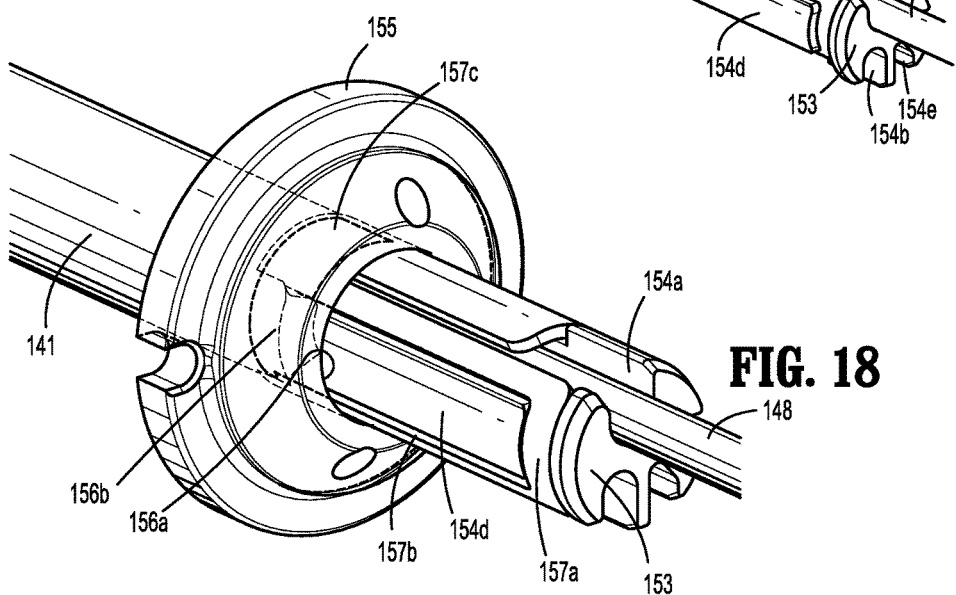
Figure 19:
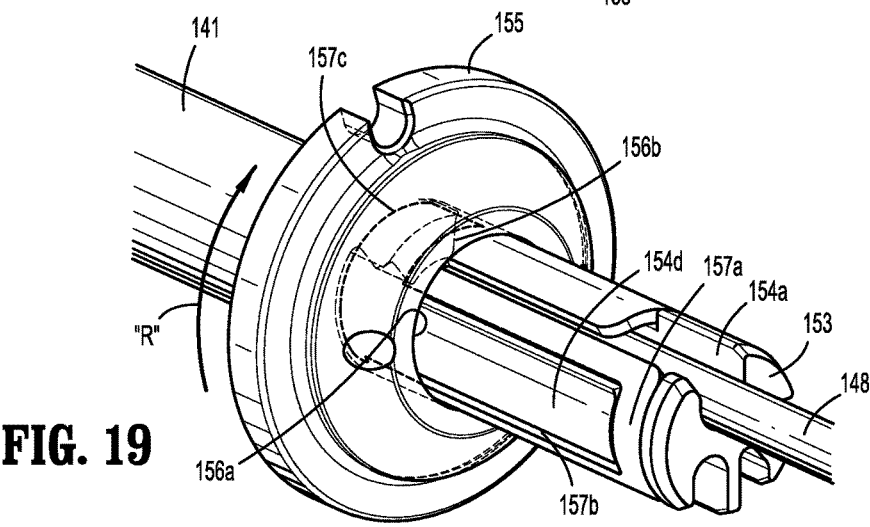
Figure 20:
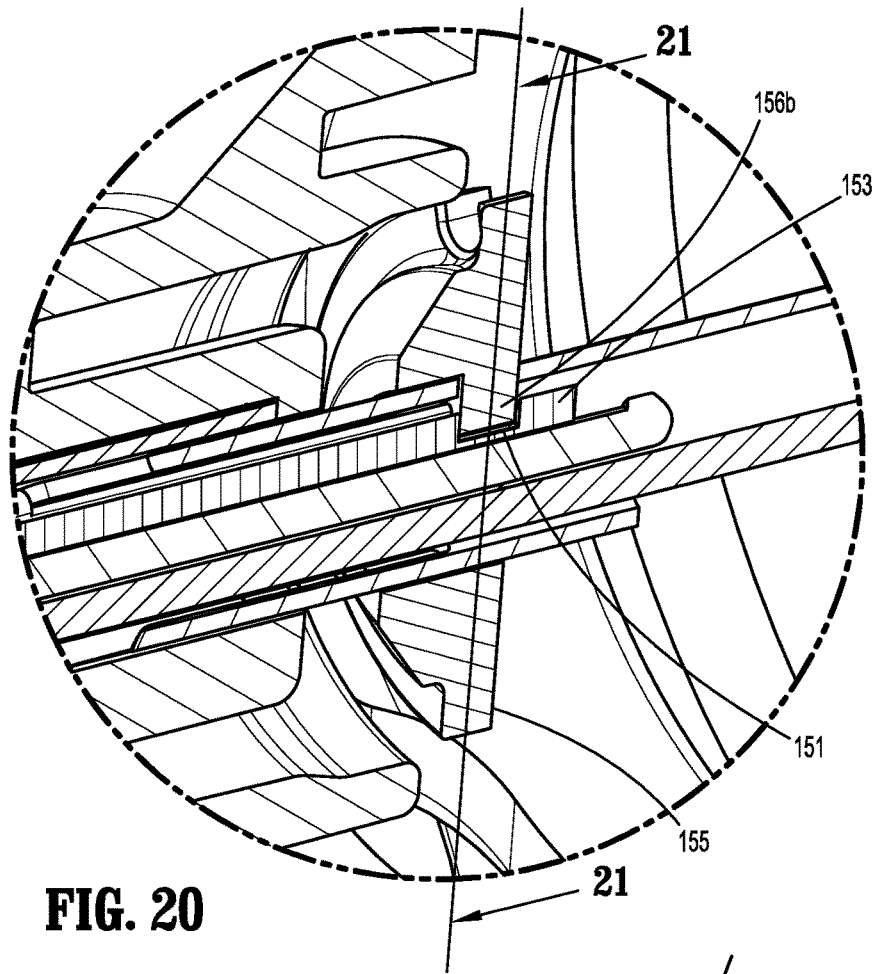
FIG. 20 is an enlarged, perspective view of the area of detail indicates as "20" in FIG. 10.

With reference to FIGS. 14 and 17, proximal sleeve 141 defines a cantilever spring arm 157a towards the distal end thereof, an elongated slot 157b defined within cantilever spring arm 157a and shaped complementary to elongated protrusion 154d of drive bar support member 153, and a semi-annular slot 157c disposed at the fixed end of cantilever spring arm 157a.

Turning to FIGS. 14 and 17-21, in order to operably couple drive bar 148 with proximal sleeve 141, the proximal end of drive bar 148 is inserted into drive bar channel 154a of drive bar support member 153 such that notch 151 and the open portion of drive bar channel 154a are oriented in similar directions, as shown in FIG. 17. Next, or prior to the insertion of the proximal end of drive bar 148 into drive bar channel 154a, return washer 155 is slid proximally about proximal sleeve 141 such that proximal sleeve 141 extends through central aperture 156a of return washer 155. More specifically, with locking finger 156b of return washer 155 aligned with cantilever spring arm 157a of drive bar support member 153, return washer 155 is slid proximally about proximal sleeve 141 (deflecting cantilever spring arm 157a inwardly at least initially), with proximal sleeve 141 extending through central aperture 156a of return washer 155 until locking finger 156b passes proximally though elongated slot 157b of proximal sleeve 141 and into semi-annular slot 157c of proximal sleeve 141 (see FIG. 18).

With return washer 155 in position as detailed above, drive bar 148 and drive bar support member 153 are advanced proximally into proximal sleeve 141 and towards return washer 155 such that cantilever spring arm 157a is flexed outwardly. Drive bar 148 and drive bar support member 153 are moved further proximally until elongated protrusion 154d of drive bar support member 153 abuts locking finger 156b of return washer 155. At this point, cantilever spring arm 157a remains outwardly-flexed.

Next, return washer 155 is rotated relative to proximal sleeve 141, drive bar 148, and drive bar support member 153 such that locking finger 156b moves through semi-annular slot 157c of proximal sleeve 141. Return washer 155 is rotated, as indicated by arrow "R" (FIG. 19), to the end of semi-annular slot 157c, such that locking finger 156b is slid into notch 151 of drive bar 148, thereby engaging drive bar 148 and return washer 155.

Once return washer 155 has been rotated as detailed above, locking finger 156b no longer abuts drive bar support member 153. Drive bar support member 153 may then be moved proximally relative to proximal sleeve 141 until elongated slot 157b defined within cantilever spring arm 157a is aligned with elongated protrusion 154d, thus allowing cantilever spring arm 157a to return inwardly under bias so as to capture elongated protrusion 154d within elongated slot 157b to engage drive bar support member 153 with proximal sleeve 141. Further, with drive bar support member 153 and proximal sleeve 141 engaged in this manner, return washer 155 is inhibited from rotating back in the opposite direction of arrow "R" (FIG. 19) due to interference between locking finger 156b and elongated protrusion 154d, and is thus retained in engagement with drive bar 148. In addition, semi-annular slot 157c inhibits longitudinal movement of return washer 155 relative to drive bar support member 153 and proximal sleeve 141. As such, as a result of the above-detailed configuration, proximal sleeve 141, drive bar 148, drive bar support member 153, and return washer 155 are fixedly engaged with one another. This assembly method obviates the need for precision joining, such as welding, to achieve proper positioning and spacing between the components.

Referring to FIGS. 1 and 4-14, drive assembly 140 further includes a biasing member 146 configured for positioning between return washer 155 and rotation wheel 72 of rotation assembly 70 so as to bias drive assembly 140 proximally. The proximal bias of drive assembly 140 biases movable handle towards the initial position. Moving movable handle 40 relative to fixed handle 50 from the initial position to the compressed position urges mandrel 144 distally. During initial movement of movable handle 40, distal movement of mandrel 144 urges biasing member 146 distally which, in turn, moves clip 145, proximal sleeve 141, drive bar 148, drive bar support member 153, and return washer 155 distally. As noted above, distal translation of drive bar 148 urges jaw member 110 to pivot relative to jaw member 120 from the spaced-apart position towards the approximated position to grasp tissue therebetween. However, when the opposing force of tissue resisting compression exceeds the spring force of biasing member 146, further movement of movable handle 40 to urge mandrel 144 distally results in compression of biasing member 146, rather than distal movement of clip 145. As such, clip 145, proximal sleeve 141, drive bar 148, drive bar support member 153, and return washer 155 are maintained in position, and jaw members 110, 120 are not further approximated. In this manner, the pressure applied to tissue grasped between jaw members 110, 120 is regulated.

Referring to FIGS. 1, 4, and 5, trigger 62 of trigger assembly 60 is selectively actuatable relative to housing 20 from an un-actuated position to an actuated position. More specifically, trigger 62 includes an intermediate portion 63 having a split pivot 64 about which trigger 62 is pivotably coupled to housing 20 on either side of housing 20. A toggle portion 65 of trigger 62 extends from split pivot 64 in a first direction, ultimately exiting housing 20 to facilitate manipulation of trigger 62 from the exterior of housing 20. A bifurcated portion 66 of trigger 62 extends from split pivot 64 in a second, opposite direction further into housing 20. Bifurcated portion 66 of trigger 62 includes a pair of spaced-apart arms 67 interconnected via a transverse pin 68.

With additional reference to FIGS. 8-13, knife assembly 160 is operably coupled to trigger 62 such that actuation of trigger 62 from the un-actuated position to the actuated position translates knife 164 of knife assembly 160 from a retracted position, wherein knife 164 is disposed proximally of jaw members 110, 120, to an extended position, wherein knife 164 extends at least partially between jaw members 110, 120 and through the knife channel(s) 126 (FIG. 12) thereof to cut tissue grasped between jaw members 110, 120.

Knife assembly 160 includes knife bar 162, knife 164, and a knife collar 166. Knife collar 166 is coaxial with mandrel assembly 142 and proximal sleeve 141 of drive assembly 140 (see FIG. 5); however knife bar 162, as noted above, extends along-side drive bar 148 (see FIG. 9) in non-coaxial, non-concentric orientation relative thereto. Knife 164 is engaged to and extends distally from knife bar 162. Knife 164 defines a sharpened distal cutting edge to facilitate cutting tissue, although other configurations are also contemplated. Knife bar 162 extends proximally from knife 164 and is configured for receipt within a channel defined within inner guide tube 86 of elongated shaft assembly 80 (see FIG. 5) such that knife bar 162 extends alongside drive bar 148, spaced-apart therefrom. Knife bar 162 extends further proximally from inner guide tube 86 for receipt within knife bar channel 154c of drive bar support member 153 and through proximal sleeve 141 of drive assembly 140. Knife bar 162 defines a proximal foot 163a that extends through an elongated cut-out 163b defined within proximal sleeve 141 (see FIG. 10).

Knife collar 166 is slidably disposed about proximal sleeve 141 of drive assembly 140. Proximal foot 163a of knife bar 162 extends through elongated cut-out 163b of proximal sleeve, as mentioned above, and is received within an annular slot 167 defined within knife collar 166 to rotatably engage knife collar 166 about the proximal end of knife bar 162 with proximal sleeve 141 of drive assembly 140 disposed therebetween. Knife collar 166 further defines a transverse aperture 168 configured to receive transverse pin 68 of trigger assembly 60 to operably couple trigger assembly 60 and knife assembly 160 with one another.

Upon actuation of trigger 62 from the un-actuated position to the actuated position, toggle portion 65 of trigger is pivoted about split pivot 64 in a generally proximal direction while bifurcated portion 66 is pivoted about split pivot 64 in a generally distal direction. Such distal movement of bifurcated portion 66 of trigger 62 urges transverse pin 68 distally, thereby urging knife collar 166 distally. Distal urging of knife collar 166 urges proximal foot 163a of knife bar 162 to translate through elongated cut-out 163b of proximal sleeve 141, thereby translating knife bar 162 and knife 164 distally relative to drive assembly 140, elongated shaft assembly 80, and end effector assembly 100 from the retracted position to the extended position to cut tissue grasped between jaw members 110, 120. In some embodiments, a biasing member (not shown) configured to bias trigger 62 towards the un-actuated position and, thus, knife 164 towards the retracted position, may be provided.

Turning to FIGS. 4, 7, 10, 13, and 22-29, rotation assembly 70 includes rotation wheel 72 that is rotatably disposed but longitudinally constrained within a vertically-oriented slot 26 defined within housing 20 (see FIG. 1). Rotation wheel 72 extends at least partially through slots 26 on either side of housing 20 to enable manipulation of rotation wheel 72 on either exterior side of housing 20 (see FIG. 1). Rotation wheel 72 is engaged about inner proximal tube 83 of elongated shaft assembly 80 such that, as mentioned above, rotation of rotation wheel 72 effects corresponding rotation of inner proximal tube 83, inner distal tube 84, inner tube guide 86, end effector assembly 100, drive assembly 140, knife assembly 160, and monopolar assembly 200 relative to housing 20 (FIG. 1) and fixed outer tube 82.

Rotation assembly 70 further includes an engagement ferrule 74, an engagement clip 76, and a retainer 78 that, as detailed below, cooperate to enable engagement of rotation wheel 72 and fixed outer tube 82 without the need for precision joining, such as welding, while ensuring accurate placement of rotation wheel 72 on inner proximal tube 83 of elongated shaft assembly 80. This positioning is important to ensure proper spacing of rotation wheel 72 relative to end effector assembly 100 such that the proper positionings, clearances, and/or ranges of motions of the various components extending through elongated shaft assembly 80 to end effector assembly 100 are achieved.

Figure 26:
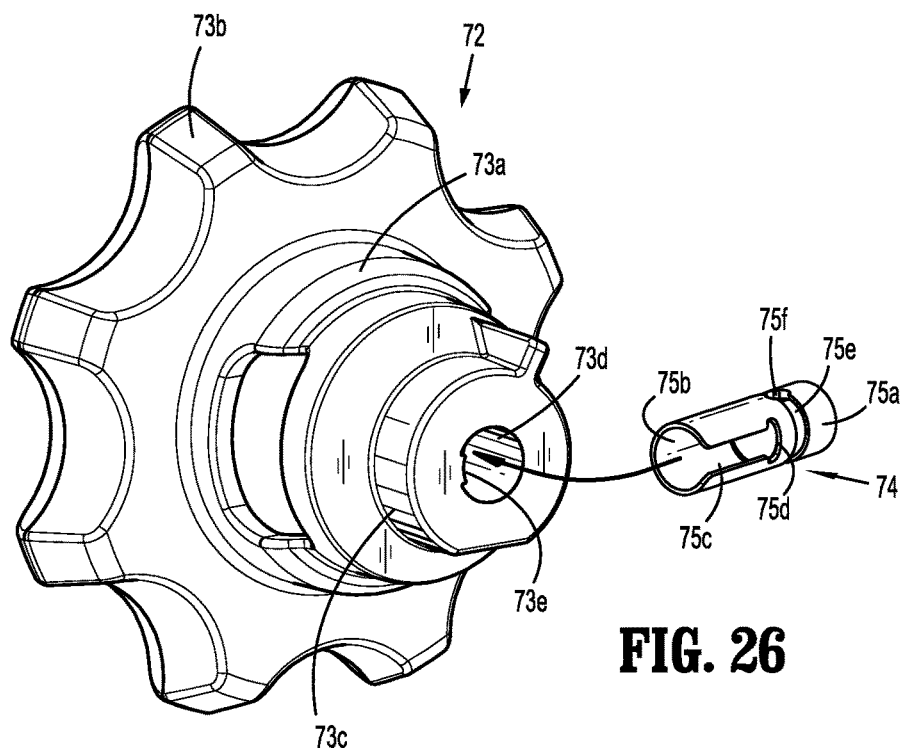
FIG. 26 is an exploded, perspective view of the proximal tube of the elongated shaft assembly of FIG. 6 and the rotation knob of the rotation assembly of FIG. 22.

Rotation wheel 72, as shown in FIG. 26, includes a body 73a having a manipulation portion 73b and a hub portion 73c and defines an aperture 73d extending therethrough. Manipulation portion 73b extends at least partially through slots 26 on either side of housing 20 to enable manipulation of rotation wheel 72. Hub portion 73c includes a raised block 73e extending inwardly into aperture 73d.

Engagement ferrule 74, as shown in FIG. 26, includes a sleeve body 75a defining a lumen 75b extending therethrough. A longitudinal slot 75c having an open proximal end and a closed distal end is defined through the outer surface of sleeve body 75a. Longitudinal slot 75c defines an enlarged locking portion 75d towards the closed distal end thereof. Longitudinal slot 75c is configured to receive raised block 73e of hub portion 73c of rotation wheel 72, as detailed below. Engagement ferrule 74 further defines an annular recess 75e and a window 75f extending through a portion of annular recess 75e into the interior of sleeve body 75a. Annular recess 75e and window 75f are disposed distally of longitudinal slot 75c.

Figure 25:
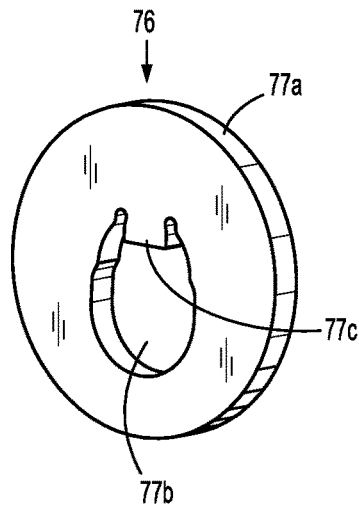
FIG. 25 is a perspective view of the clip of the drive assembly of FIG. 22.

Engagement clip 76, as shown in FIG. 25, defines a disc-shaped body 77a having an irregular aperture 77b extending therethrough. A tab 77c extends from disc-shaped body 77a into irregular aperture 77b.

Figure 24:
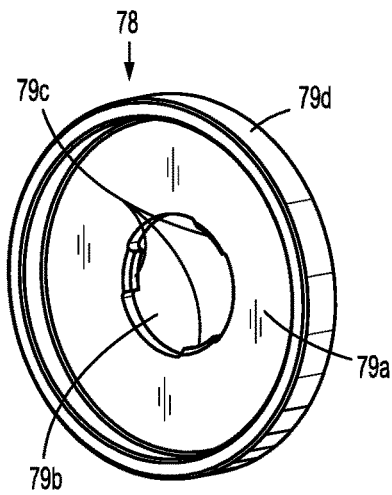
FIG. 24 is a perspective view of the retainer of the drive assembly of FIG. 22.

Retainer 78, as shown in FIG. 24, defines a disc-shaped body 79a configured similar to or slightly larger than disc-shaped body 77a of engagement clip 76 (FIG. 25). Disc-shaped body 79a defines an aperture 79b therethrough and includes a plurality of spaced-apart tabs 79c extending inwardly into aperture 79b. Tabs 79c may be equally-spaced annularly about aperture 79b, as shown in FIG. 24, or may define any other suitable configuration. Retainer 78 further includes a collar 79d disposed about the outer periphery of disc-shaped body 79a. Collar 79d, as detailed below, is configured to surround disc-shaped body 77a of engagement clip 76 (FIG. 25) so as to engage retainer about engagement clip 76 (FIG. 25) with disc-shaped bodies 77a (FIG. 25), 79a adjacent one another.

Referring to FIGS. 22-29, the assembly of rotation wheel 72 on inner proximal tube 83 of elongated shaft assembly 80 is detailed. Initially, as shown in FIG. 26, engagement ferrule 74 is inserted into aperture 73d of rotation wheel 72 with raised block 73e of rotation wheel 72 aligned with longitudinal slot 75c of engagement ferrule 74. More specifically, upon insertion of engagement ferrule 74 into aperture 73d of rotation wheel 72, sleeve body 75a is deflected so as to enlarge longitudinal slot 75c and enable passage of raised block 73e therethrough. Upon sufficient insertion of engagement ferrule 74 into aperture 73d of rotation wheel 72, raised block 73e reaches enlarged locking portion 75d of longitudinal slot 75c, allowing sleeve body 75a to return to an at-rest, un-deflected position, thereby retaining raised block 73e within enlarged locking portion 75d of longitudinal slot 75c and, thus, engaging engagement ferrule 74 with rotation wheel 72.

Figure 22:
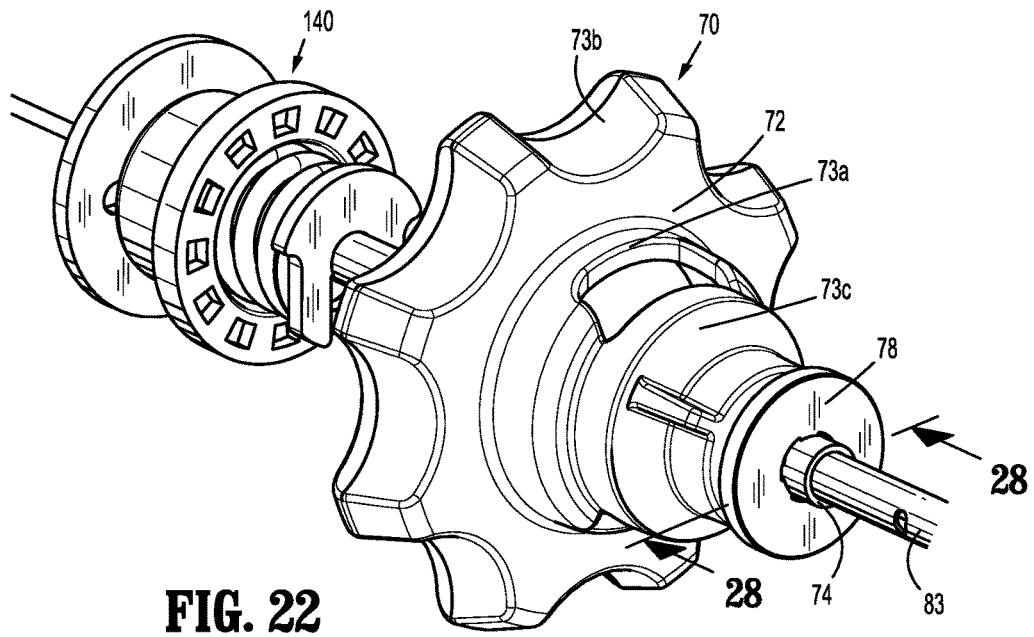
FIG. 22 is a perspective view of the rotation assembly and the drive assembly of the surgical instrument of FIG. 1.
Figure 23:
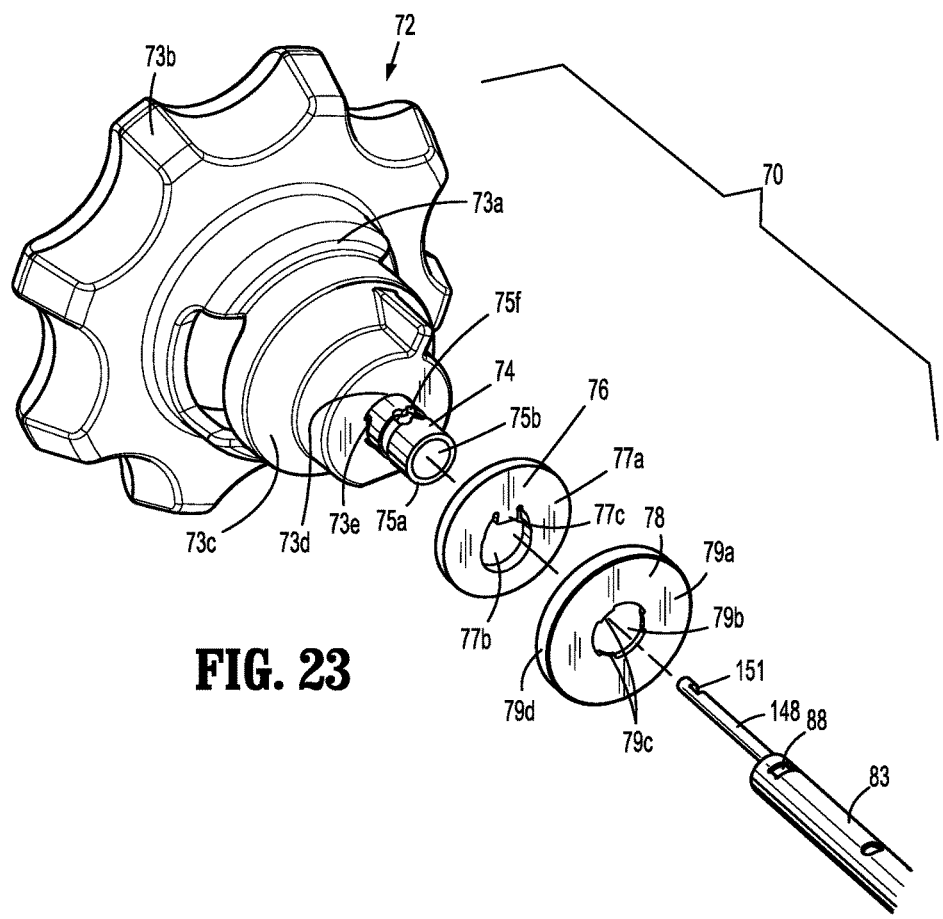
FIG. 23 is an exploded, perspective view of the rotation assembly and a portion of the drive assembly of FIG. 22.
Figure 27:
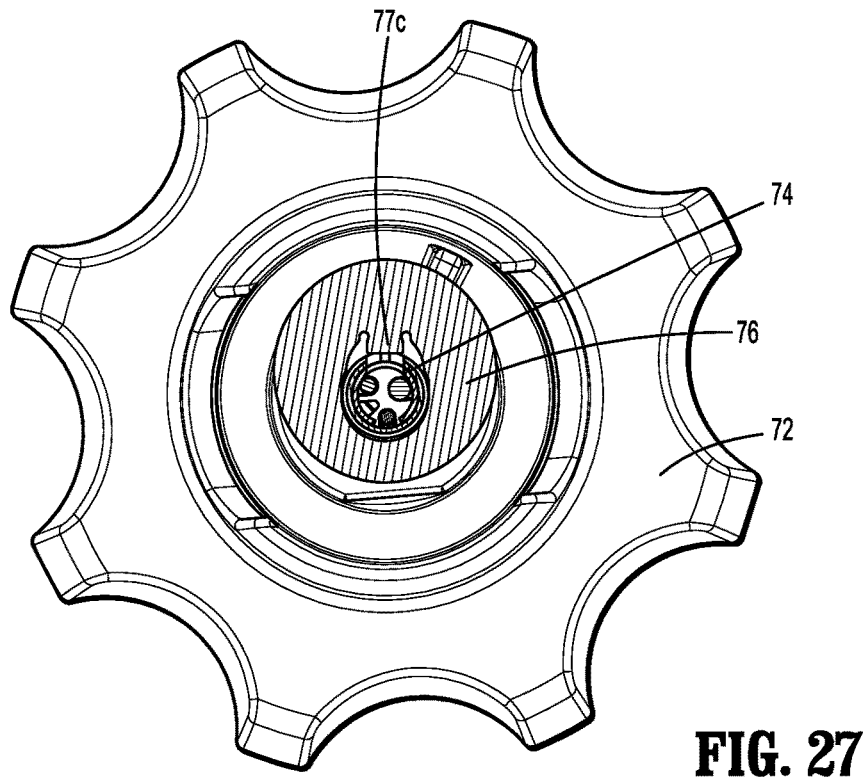
FIG. 27 is a cross-sectional view taken across section line "28-28" in FIG. 22, except that the clip of the elongated shaft assembly is disengaged.
Figure 28:
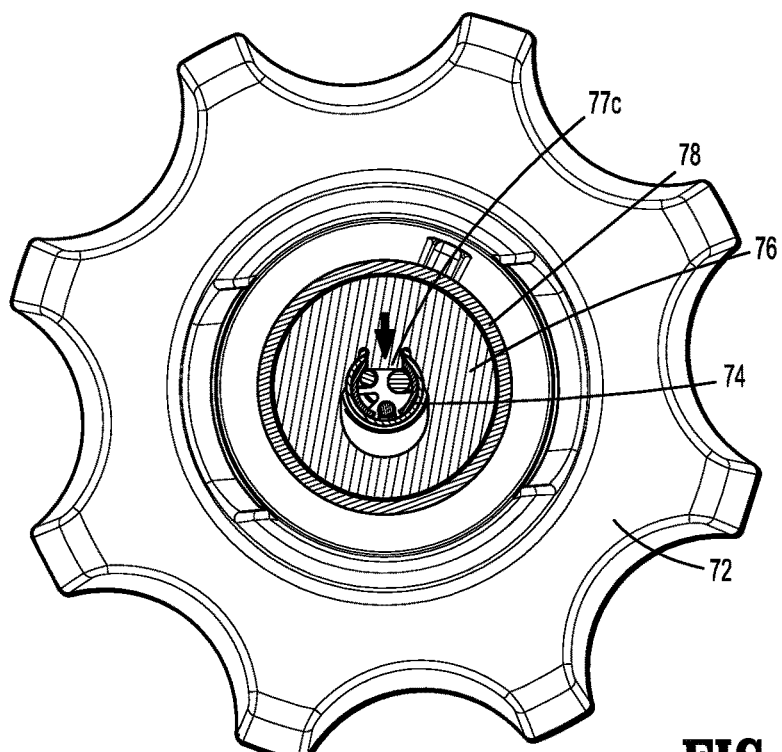
FIG. 28 is a cross-sectional view taken across section line "28-28" in FIG. 22, wherein the clip of the elongated shaft assembly is engaged.

Referring to FIGS. 22 and 23, once engagement ferrule 74 is engaged with rotation wheel 72, as detailed above, inner proximal tube 83 of elongated shaft assembly 80 is translated proximally through aperture 79b of retainer 78, irregular aperture 77b of engagement clip 76, and into engagement ferrule 74 such that window 88 defined through inner proximal tube 83 is aligned with window 75f defined within engagement ferrule 74. Thereafter, engagement clip 76 is translated proximally about inner proximal tube 83 and engagement ferrule 74 until tab 77c is aligned above windows 75f, 88, as shown in FIG. 27. Once tab 77c is aligned with windows 75f, 88, engagement clip 76 is moved transversely relative to inner proximal tube 83 and engagement ferrule 74 such that tab 77c extends through windows 75f, 88, thereby engaging inner proximal tube 83 and engagement ferrule 74 with one another, as shown in FIG. 28.

Figure 29:
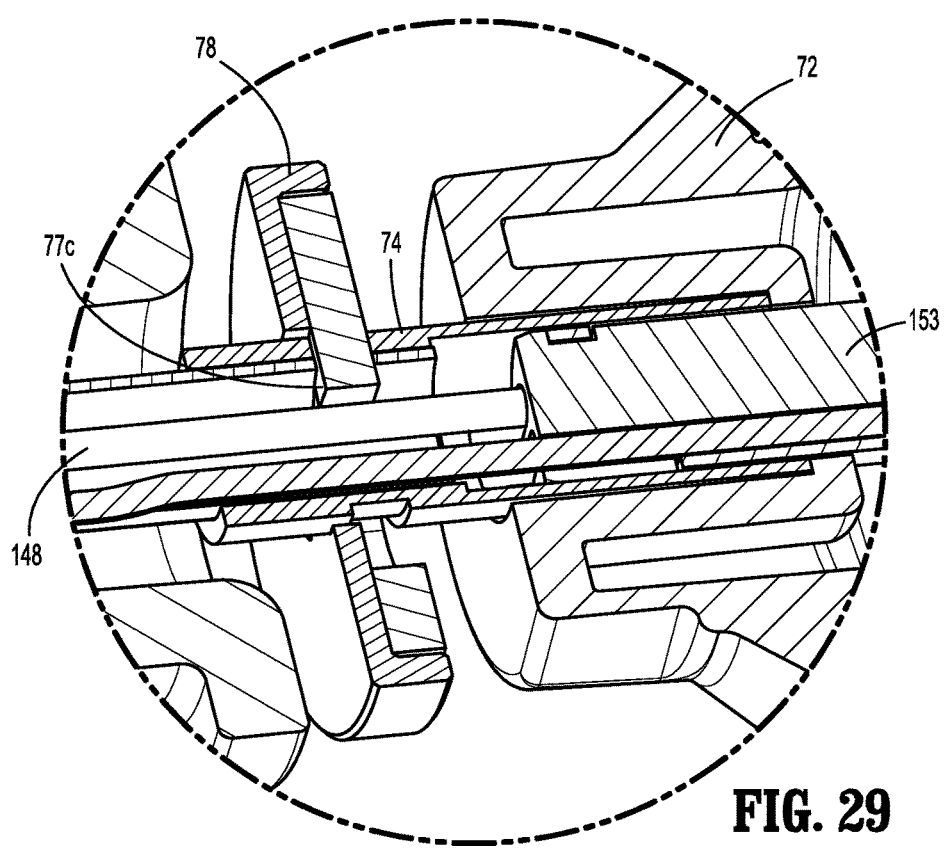
FIG. 29 is an enlarged, cross-sectional view of the area indicated as "29" in FIG. 13.

With reference to FIG. 29, in order to secure the engagement between engaging inner proximal tube 83 and engagement ferrule 74, retainer 78 is slid proximally about inner proximal tube 83 and engagement ferrule 74 until collar 79d of retainer 78 is engaged about disc-shaped body 77a of engagement clip 76 to inhibit engagement clip 76 from backing-out of engagement with inner proximal tube 83 and engagement ferrule 74. Simultaneously with or near in time to this engagement of collar 79d about disc-shaped body 77a, spaced-apart tabs 79c of retainer 78 are engaged, e.g., via snap-fit engagement, within annular recess 75e of engagement ferrule 74 to thereby lock retainer 78 in position. This completes the assembly of rotation wheel 72 to inner proximal tube 83.

Figure 30:
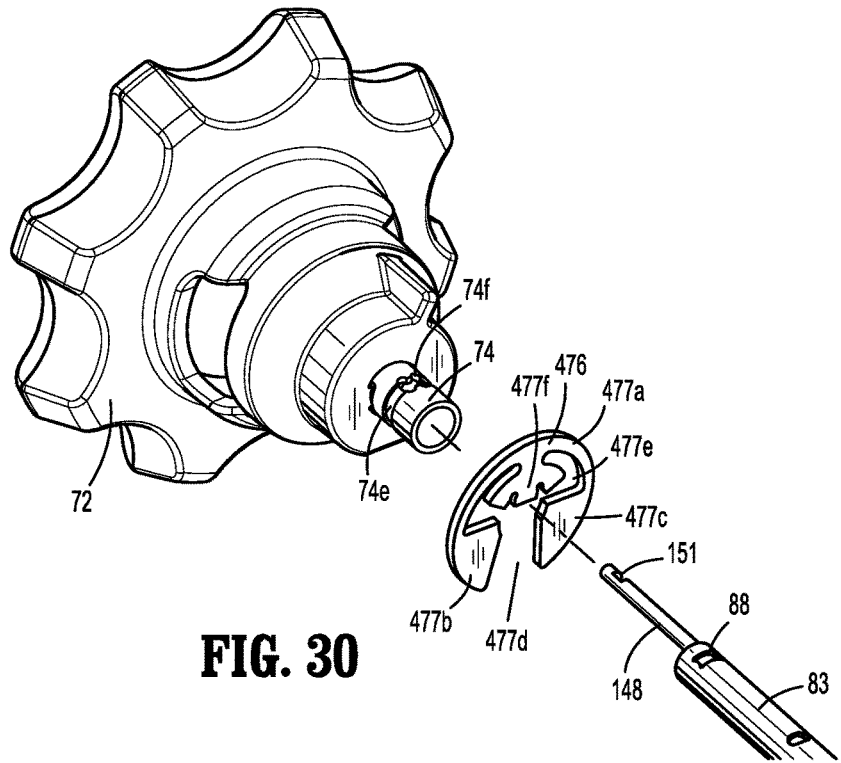
FIG. 30 is an exploded, perspective view of the drive assembly and rotation assembly of the surgical instrument of FIG. 1 with another clip configured to facilitate engagement therebetween.
Figure 31:
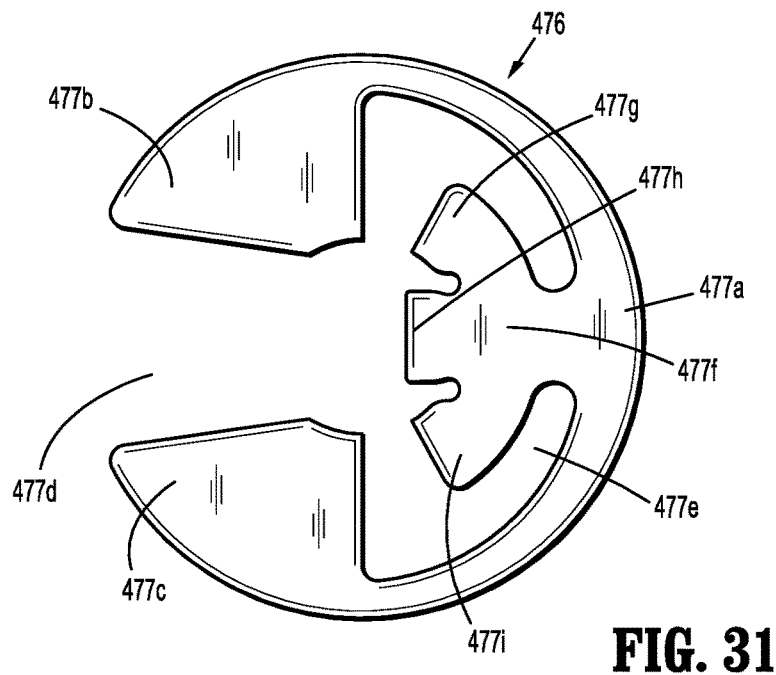
FIG. 31 is a side view of the clip of FIG. 30.
Figure 32:
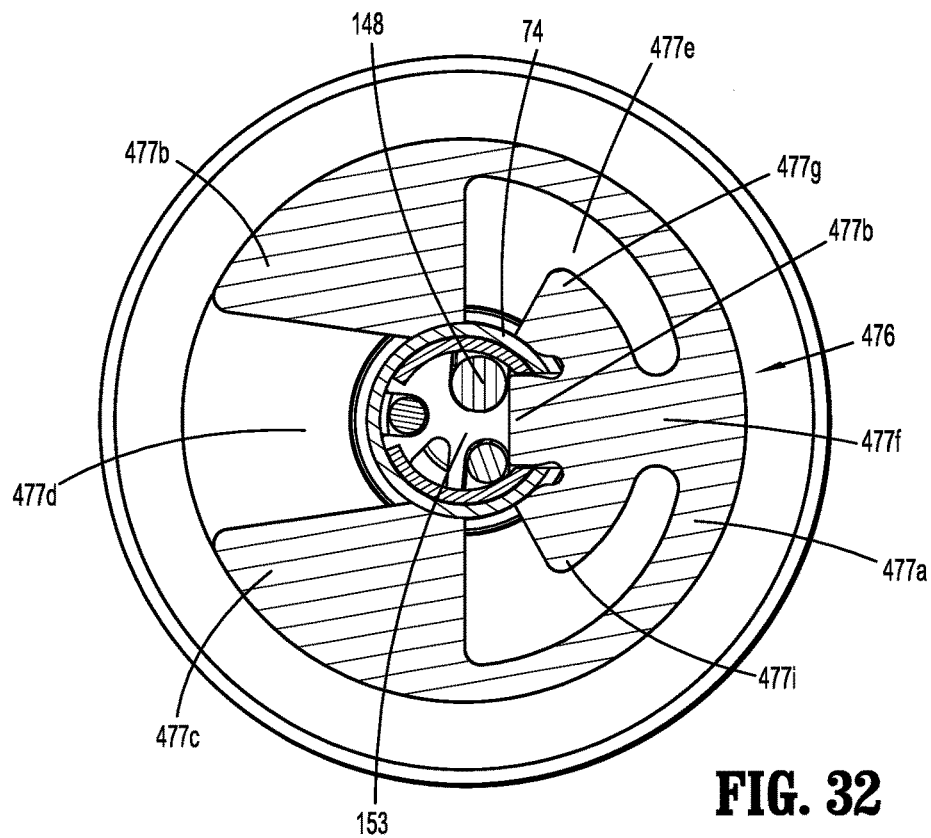
FIG. 32 is a cross-sectional view illustrating the clip of FIG. 30 engaging the drive assembly and rotation assembly with one another.

Turning to FIGS. 30-32, another configuration for assembling rotation wheel 72 on inner proximal tube 83 of elongated shaft assembly 80 is detailed. More specifically, in the configuration illustrated in FIGS. 30-32, rather than using engagement clip 76 and retainer 78 (see FIG. 23), a G-clip 476 is utilized. G-clip 476 includes a body 477*a* defining a pair of semi-annular cantilever arms 477*b*, 477*c*. The free ends of arms 477*b*, 477*c* define a gap 477*d* therebetween. Body 477*a* further defines a window 477*e* towards the fixed ends of arms 477*b*, 477*c*. A hand 477*f* including three spaced-apart fingers 477*g*, 477*h*, 477*i* extends from body 477*a* into window 477*e* between arms 477*b*, 477*c*.

Assembly using G-clip 476 is initially similar to that detailed above. That is, engagement ferrule 74 is first engaged with rotation wheel 72, and then inner proximal tube 83 of elongated shaft assembly 80 is inserted into engagement ferrule 74 such that window 88 defined through inner proximal tube 83 is aligned with window 75*f* defined within engagement ferrule 74. Once this position has been achieved, G-clip 476 is inserted about engagement ferrule 74 transversely. That is, G-clip 476 is urged transversely about engagement ferrule 74 such that engagement ferrule 74 urges cantilever arms 477*b*, 477*c* outwardly relative to one another to widen gap 477*d* and permit insertion of engagement ferrule 74 therethrough. G-clip 476 is moved further transversely relative to engagement ferrule 74 such that middle finger 477*h* of hand 477*f* extends through windows 75*f*, 88, thereby engaging inner proximal tube 83 and engagement ferrule 74 with one another. Upon reaching this position, the inward bias of arms 477*b*, 477*c* into contact with engagement ferrule 74 retains G-clip 476 about engagement ferrule 74, while outer fingers 477*g* and 477*i* are biased inwardly into engagement within annular recess 75*e* of engagement ferrule 74 to retain middle finger 477*h* in engagement with windows 75*f*, 88. This completes the assembly of rotation wheel 72 to inner proximal tube 83 using G-clip 476.

With reference to FIGS. 1-5, monopolar assembly 200 includes an insulative sheath 210 and an energizable member 220. Insulative sheath 210 defines a body portion 217 and an enlarged-diametered distal portion 218 extending distally from body portion 217. An annular step 219 is defined at the interface between body portion 217 and enlarged-diametered distal portion 218 of insulative sheath 210. Insulative sheath 210 is movable relative to end effector assembly 100 between a storage position, wherein insulative sheath 210 is disposed proximally of end effector assembly 100, and a use position, wherein insulative sheath 210 is substantially disposed about end effector assembly 100.

Energizable member 220 of monopolar assembly 200 includes a proximal cap 222, a bar 224, and an energizable element 226. Proximal cap 222 is engaged to bar 224 at the proximal end thereof and is operably engaged with deployment and retraction mechanism 300 for selectively deploying and retracting monopolar assembly 200. Bar 224 extends from proximal cap 222 distally through housing 20. Energizable element 226 extends through proximal bar 224 and distally therefrom to a distal tissue-treating portion 227. Energizable element 226 is coupled to the source of energy (not shown) and monopolar activation assembly 180 (FIG. 5) via one or more wires (not shown). Distal tissue-treating portion 227 of energizable element 226 of energizable member 220 functions as the active electrode of monopolar assembly 200. Distal tissue-treating portion 227 may be hook-shaped (as shown), or may define any other suitable configuration, e.g., linear, ball, circular, angled, etc. Proximal bar 224 is insulated so as to facilitate the electrical insulation of energizable element 226 from its surroundings.

Figure 21:
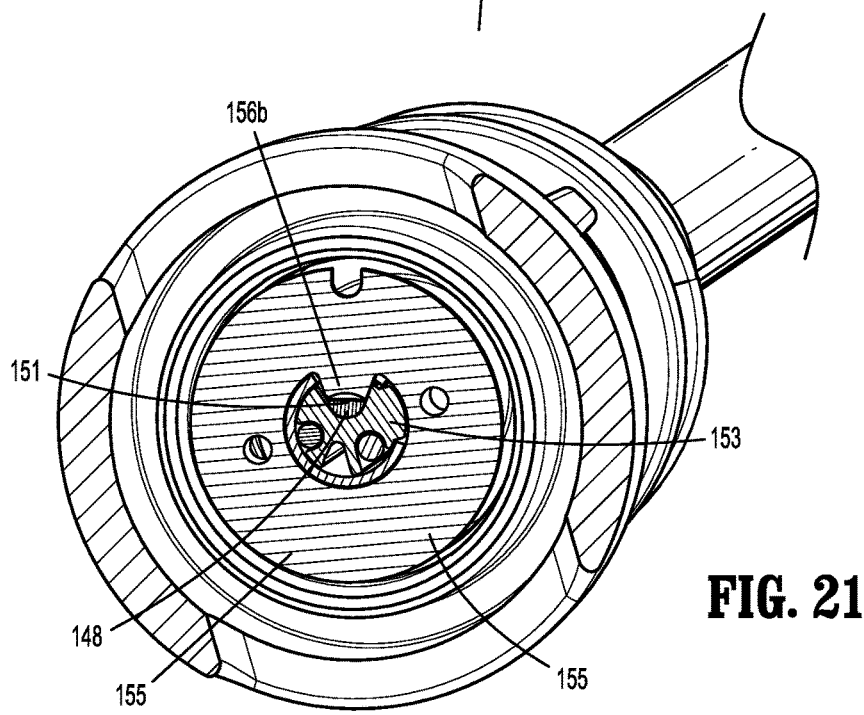
FIG. 21 is a cross-sectional view taken along section line "21-21" of FIG. 20.

Energizable member 220 slidably extends through a channel defined within inner guide tube 86 of elongated shaft assembly 80 (see FIG. 5) and energizable member channel 154*b* of drive bar support member 153 (see FIG. 21).

Referring to FIG. 2, energizable member 220 is disposed on the inner-edge side of jaw members 110, 120 of end effector assembly 100 and is movable relative thereto between a storage position, wherein distal tissue-treating portion 227 of energizable member 220 is positioned more-proximally, and a use position, wherein distal tissue-treating portion 227 of energizable member 220 extends distally from end effector assembly 100 to facilitate treating tissue therewith. In the use position, insulative sheath 210 serves to electrically insulate end effector assembly 100 from distal tissue-treating portion 227 of energizable member 220, while distal tissue-treating portion 227 extends distally from end effector assembly 100. Further, in the use position, energy may be supplied to distal tissue-treating portion 227 of energizable member 220, e.g., via activation of either of the activation switches 182 of monopolar activation assembly 180 (FIG. 1), for treating tissue in the monopolar mode of operation.

Referring also to FIGS. 4 and 5, energizable member 220 is engaged with insulative sleeve 210 such that energizable member 220 and insulative sleeve 210 move together between their respective storage and use positions. Further, proximal cap 222 of energizable member 220 is operably coupled to deployment and retraction mechanism 300, thus enabling deployment and retraction mechanism 300 to translate insulative sheath 210 and energizable member 220 between their respective storage positions, collectively the storage condition of monopolar assembly 200, and their respective use conditions, collectively the use condition of monopolar assembly 200. A more detailed description of monopolar assembly 200, deployment and retraction mechanism 300, and the various safety features associated therewith can be found in U.S. patent application Ser. No. 14/802,582 to Anglese et al., filed on Jul. 17, 2015, the entire contents of which are hereby incorporated herein by reference.

Turning to FIGS. 33-40, another configuration of inner proximal and distal tubes 483, 484 of elongated shaft assembly 80 is shown. Inner proximal and distal tubes 483, 484 are similar to respective inner proximal and distal tubes 83, 84 (FIG. 5), except that inner proximal and distal tubes 483, 484 include cut-outs 485, 486 so as to define C-shaped configurations. The C-shaped configurations of inner proximal and distal tubes 483, 484 and, more specifically, cut-outs 485, 486 thereof, allow for additional spacing to accommodate all of the components extending therethrough. For example, as shown in FIGS. 38-40, energizable member 220 may extend through elongated shaft assembly 80 at least partially within cut-outs 485, 486, rather than being required to be fully disposed within the interior of inner proximal and distal tubes 483, 484. Referring to FIG. 40, this configuration enables movement of energizable member 220 further outwardly relative from the position indicated by the phantom energizable member 220'.

Referring to FIG. 1, the use and operation of instrument 10 is similar to that described in U.S. patent application Ser. No. 14/802,582, previously incorporated herein by reference, except that instrument 10 provides the further benefit of permitting deployment and retraction of monopolar assembly 200 (FIG. 2) between the storage condition and the use condition even when elongated shaft assembly 80 is bent off-axis. Such a situation may arise, for example, when instrument 10 is inserted through a trocar (not shown), or other spatially-constrained device or area, and the surgeon is attempting to manipulate instrument 10 to a desired position. As noted above, bending of elongated shaft assembly 80 up to about 35 degrees off-axis is permitted without limiting deployment and retraction of monopolar assembly 200 (FIG. 2). Manipulation of end effector assembly 100 and deployment of knife 164 (FIG. 5) may likewise be effected without limitation when elongated shaft assembly 80 is bent off-axis up to about 35 degrees.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing;
first, second, and third actuators operably coupled to the housing;
a shaft extending distally from the housing, at least a portion of the shaft defining a semi-rigid configuration enabling the shaft to be bent at an angle of up to 35 degrees without permanent deformation or breaking;
a rotation assembly positioned in the housing, the rotation assembly including an engagement ferrule positioned about a proximal portion of the shaft, the engagement ferrule including a recess formed at least partially around the engagement ferrule;
an engagement clip engaged with an outer surface of the engagement ferrule in the recess, the engagement clip including at least one protrusion configured to fix the proximal portion of the shaft to the engagement ferrule;
an end effector assembly disposed at a distal end of the shaft; and
first, second, and third bars extending through the shaft and disposed in non-coaxial arrangement relative to each other and the shaft, the first bar operably coupled between the first actuator and the end effector assembly such that actuation of the first actuator effects manipulation of the end effector assembly, the second bar operably coupled between the second actuator and a first deployable component such that actuation of the second actuator effects deployment of the first deployable component relative to the end effector assembly, the third bar operably coupled between the third actuator and a second deployable component such that actuation of the third actuator effects deployment of the second deployable component relative to the end effector assembly,
wherein the first, second, and third actuators are actuatable to manipulate the end effector assembly, deploy the first deployable component, and deploy the second deployable component, respectively, with the shaft bent at an angle of up to 35 degrees from a longitudinal axis thereof.

2. The surgical instrument according to claim 1, wherein the end effector assembly includes first and second jaw members adapted to connect to a source of energy for conducting energy through tissue, at least one of the first or second jaw members movable relative to the other between a spaced-apart position and an approximated position for grasping tissue therebetween.

3. The surgical instrument according to claim 2, wherein the first actuator includes a movable handle operably coupled to the housing, the movable handle movable relative to the housing from an initial position to a compressed position to move the at least one of the first or second jaw members from the spaced-apart position to the approximated position.

4. The surgical instrument according to claim 1, wherein the first deployable component is a knife selectively deployable between the first and second jaw members to cut tissue grasped therebetween.

5. The surgical instrument according to claim 4, wherein the second actuator includes a trigger operably coupled to the housing, the trigger movable relative to the housing from an un-actuated position to an actuated position to deploy the knife between the first and second jaw members.

6. The surgical instrument according to claim 1, wherein the second deployable component includes an energizable member configured to conduct energy to tissue, the energizable member movable relative to the end effector assembly between a retracted position, wherein the energizable member is positioned more-proximally, and an extended position, wherein the energizable member extends distally from the end effector assembly.

7. The surgical instrument according to claim 6, further comprising an insulative sleeve coupled to the energizable member and movable therewith, the insulative sleeve disposed proximally of the end effector assembly in the retracted position, and disposed about the end effector assembly in the extended position.

8. The surgical instrument according to claim 1, further comprising a proximal sleeve operably coupling the first actuator and the first bar, wherein the proximal sleeve and the shaft are co-axial.

9. The surgical instrument according to claim 8, further comprising a guide member engaging the proximal sleeve and the first bar.

10. The surgical instrument according to claim 9, wherein the guide member defines a first guide channel configured to retain a portion of the first bar, a second guide channel configured to slidably receive the second bar, and a third guide channel configured to slidably receive the third bar.

11. The surgical instrument according to claim 9, further comprising a washer operable to retain the guide member, proximal sleeve, and first bar in engagement with one another.

12. The surgical instrument according to claim 8, further comprising a mandrel assembly disposed about the proximal sleeve, the mandrel assembly operably coupling the first actuator and the proximal sleeve, wherein the mandrel assembly, the proximal sleeve, and the shaft are co-axial.

13. The surgical instrument according to claim 1, further comprising a collar operably coupling the second actuator and the second bar, wherein the collar and the shaft are co-axial.

14. The surgical instrument according to claim 1, wherein the shaft includes at least one support segment, the at least one support segment defining a first support channel for slidably receiving the first bar, a second support channel for slidably receiving the second bar, and a third support channel for slidably receiving the third bar.

15. The surgical instrument according to claim 1, wherein at least a portion of the shaft defines a cut-out therethrough, and wherein at least one of the first, second, or third bars extends at least partially into the cut-out.

16. The surgical instrument according to claim 1, wherein the rotation assembly is operably coupled to the first, second, and third bars such that rotation of the rotation assembly relative to the housing rotates the shaft, the end effector assembly, the first, second, and third bars, and the first and second deployable components relative to the housing.

17. The surgical instrument according to claim 1, further comprising a fixed outer tube disposed about the shaft, wherein the fixed outer tube and the shaft are co-axial.

18. The surgical instrument according to claim 17, further comprising an insulative sleeve slidably disposed between the fixed outer tube and the shaft, wherein the insulative sleeve, fixed outer tube, and shaft are co-axial.

* * * * *